United States Patent
Coates et al.

(10) Patent No.: US 10,214,614 B2
(45) Date of Patent: Feb. 26, 2019

(54) COPOLYMERIZATION OF ETHYLENE OXIDE AND CARBON DIOXIDE

(71) Applicant: Cornell University, Ithaca, NY (US)

(72) Inventors: Geoffrey W. Coates, Lansing, NY (US); Scott Allen, Ithaca, NY (US); Tsuyoshi Ando, Ikoma (JP)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/627,733

(22) Filed: Feb. 20, 2015

(65) Prior Publication Data
US 2015/0353680 A1  Dec. 10, 2015

Related U.S. Application Data

(63) Continuation of application No. 13/915,320, filed on Jun. 11, 2013, now abandoned, which is a
(Continued)

(51) Int. Cl.
*C08G 64/00* (2006.01)
*C08G 64/34* (2006.01)
(Continued)

(52) U.S. Cl.
CPC ............ *C08G 64/34* (2013.01); *C07F 15/065* (2013.01); *C08G 64/0208* (2013.01); *C08G 64/183* (2013.01)

(58) Field of Classification Search
CPC .................................................. C08G 64/00
(Continued)

(56) References Cited

U.S. PATENT DOCUMENTS 684,961 A    10/1901 Vonderahe
5,266,283 A  11/1993 Friesen et al.
(Continued)

FOREIGN PATENT DOCUMENTS

CN    2007 1010706    1/2007
CN    1887934 A       1/2007
(Continued)

OTHER PUBLICATIONS

Allen, S.D. et al., High-Activity, Single-Site Catalysts for the Alternating Copolymerization of $CO_2$ and Propylene Oxide, Journal of the American Chemical Society, 124:14284-14285 (2002).
(Continued)

*Primary Examiner* — Duc Truong
(74) *Attorney, Agent, or Firm* — Choate Hall & Stewart LLP; Charles E. Lyon; Michael A. Shinall

(57) ABSTRACT

The present disclosure is directed, in part, to methods of synthesizing a poly(ethylene carbonate) polymer from the reaction of ethylene oxide (EO) and carbon dioxide ($CO_2$) in the presence of a metal complex. The present disclosure also provides novel metal complexes. In one aspect, the metal complex is of the formula (I), wherein $R^1$, $R^2$, $R^3$, M, X and Ring A are as defined herein.

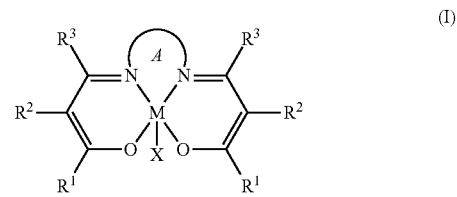

25 Claims, 4 Drawing Sheets

Related U.S. Application Data continuation of application No. 12/990,202, filed as application No. PCT/US2009/042926 on May 6, 2009, now abandoned.

(60) Provisional application No. 61/052,061, filed on May 9, 2008.

(51) Int. Cl.

| | | |
|---|---|---|
| *C07F 15/06* | (2006.01) | |
| *C08G 64/02* | (2006.01) | |
| *C08G 64/18* | (2006.01) | |
| *C07F 15/00* | (2006.01) | |
| *C07F 5/00* | (2006.01) | |

(58) Field of Classification Search
USPC .............................................. 528/405; 556/1
See application file for complete search history.

(56) References Cited

U.S. PATENT DOCUMENTS

| | | |
|---|---|---|
| 5,637,739 A | 6/1997 | Jacobsen et al. |
| 5,663,393 A | 9/1997 | Jacobsen et al. |
| 5,665,890 A | 9/1997 | Jacobsen et al. |
| 5,929,232 A | 7/1999 | Jacobsen et al. |
| 6,130,340 A | 10/2000 | Jacobsen et al. |
| 6,309,997 B1 | 10/2001 | Fujita et al. |
| 6,639,087 B2 | 10/2003 | Larrow et al. |
| 6,844,448 B2 | 1/2005 | Jacobsen et al. |
| 6,884,750 B2 | 4/2005 | Kim et al. |
| 6,903,043 B2 | 6/2005 | Kim et al. |
| 7,145,022 B2 | 12/2006 | Luinstra et al. |
| 7,244,805 B2 | 7/2007 | Park et al. |
| 7,268,204 B2 | 9/2007 | Hinz et al. |
| 7,304,172 B2 | 12/2007 | Coates et al. |
| 8,163,867 B2 | 4/2012 | Lee et al. |
| 8,207,365 B2 | 6/2012 | Zheng et al. |
| 8,232,267 B2 | 7/2012 | Groves |
| 8,252,955 B2 | 8/2012 | Gao et al. |
| 8,461,290 B2 | 6/2013 | Carpentier et al. |
| 8,507,733 B2 | 8/2013 | Ok et al. |
| 8,598,309 B2 | 12/2013 | Jeong et al. |
| 8,642,721 B2 | 2/2014 | Ok et al. |
| 8,791,274 B2 | 7/2014 | Ok et al. |
| 2008/0108499 A1 | 5/2008 | Coates et al. |
| 2010/0256329 A1 | 10/2010 | Nozaki et al. |
| 2011/0087001 A1 | 4/2011 | Coates et al. |
| 2014/0066591 A1 | 3/2014 | Coates et al. |
| 2014/0249279 A1 | 9/2014 | Williams et al. |

FOREIGN PATENT DOCUMENTS

| | | |
|---|---|---|
| CN | 101020747 A | 8/2007 |
| CN | 101029130 A | 9/2007 |
| CN | 100384909 C | 4/2008 |
| CN | 101367924 A | 2/2009 |
| EP | 0803532 A1 | 10/1997 |
| EP | 0864361 A2 | 9/1998 |
| EP | 2002-28775 | 12/2002 |
| EP | 2146977 B1 | 11/2012 |
| EP | 2257559 B1 | 10/2014 |
| JP | 54038397 | 3/1979 |
| JP | 54040599 | 12/1979 |
| JP | 07247351 | 9/1995 |
| JP | 09151192 | 6/1997 |
| JP | 09235362 | 9/1997 |
| JP | 09235364 | 9/1997 |
| JP | 09235376 | 9/1997 |
| JP | 09235377 | 9/1997 |
| JP | 2006/241247 A | 9/2006 |
| JP | 2009-215529 A | 9/2009 |
| WO | WO-98/04538 A1 | 2/1998 |
| WO | WO-9911694 A1 | 3/1999 |
| WO | WO-2002-079136 A1 | 10/2002 |
| WO | WO-03/029240 A1 | 4/2003 |
| WO | WO-2007-129525 A1 | 11/2007 |
| WO | WO-2008/136591 A1 | 11/2008 |
| WO | WO-2009/137540 A1 | 11/2009 |
| WO | WO-2010/022388 A1 | 2/2010 |
| WO | WO-2010/028362 A1 | 3/2010 |
| WO | WO-2010/033703 A1 | 3/2010 |

OTHER PUBLICATIONS

Cheng, M. et al., Catalytic Reactions Involving C1 Feedstocks: New High-Activity Zn(II)-Based Catalysts for the Alternating Copolymerization of Carbon Dioxide and Epoxides, Journal of American Chemical Society, 120:11018-11019 (1998).

Cheng, M. et al., Single-Site β-Diiminate Zinc Catalysts for the Alternating Copolymerization of CO2 and Epoxides: Catalyst Synthesis and Unprecedented Polymerization Activiy, Journal of American Chemical Society, 121:8738-8749 (2001).

Coates, G.W. and Moore, D.R., Discrete Metal-Based Catalysts for the Copolymerization of $CO_2$ and Epozides: Discovery, Reactivity, Optimization, and Mechanism, Angewandte Chemie International Edition, 43:6618-6639 (2004).

Cohen, C. et al., Copolymerization of cyclohexene oxide and carbon dioxide using (salen)Co(III)complexes: synthesis and characterization of syndiotactic poly(cyclohexene carbonate), The Royal Society of Chemistry, Dalton Trans. 237-249 (2006).

Cohen, C.T. et al., Cobalt Catalysts for the Alternating Copolymerization of Propylene Oxide and Carbon Dioxide: Combining High Activity and Selectivity, Journal of the American Chemical Society, 127:10869-10878 (2005).

Cohen, G.W. and Moore, D.R., Alternating Copolymerization of Propylene Oxide and Carbon Dioxide with Highly Efficient and Selective (Salen)CO(III) Catalysts: Effect of Ligand and Cocatalyst Variation, Journal of Polymer Science, 44:5182-5191 (2006).

Darensbourg, D.J. and Holtcamp, M.W., Catalysts for the reactions of epoxides and carbon dioxide, Coordination Chemistry Review, 153:155-174 (1996).

European Office Action for EP 09743526.7, dated Aug. 24, 2012, 3 pages.

European Third Party Observation pursuant to Aricle 115EP for EP09743526.7, 2 pages (dated Apr. 25, 2012).

European Third Party Observation pursuant to Article 115 EPC for EP2285864, 49 pages (dated May 25, 2011).

Gregson, C.K.A. et al, Titanium-salen complexes as initiators for the ring opening polymerisation of rac-lactide, Dalton Transactions, 3134-3140 (2006).

Hirsch, J.A., Table of Conformational Engergies, Topics in Stereochemistry, 1:199-222 (1967).

Hongfa, C. et al., A phase separable polycarbonate polymerization catalyst, The Royal Society of Chemistry, 975-977 (2008).

International Search Report for PCT/US2009/042926, 7 pages (dated Jul. 24, 2009).

Jensen, F.R. and Bushweller, C.H., Conformational Preferences in Cyclohexanes and Cyclohexenes, Advances in Alicyclic Chemistry, 3:139-194 (1967).

Jing, H. et al., Ruthenium Salen/phenyltrimethylammonium tribromide catalyzed coupling reaction of carbon dioxide and epoxides, Catalysis Communications, 8(11):1630-1634 (2007).

Jing, L. et al., Chiral catalysts for the asymmetric cycloaddition of carbon dioxide with epoxides, Tetrahedron: *Asymmetry*, 19(16):1947-1953 (2008).

Kashanian, S. et al., DNA interaction with Al-N,N'-bis(salicylidene)2,2'-phenylendiamine complex, Spectrochimica Acta Part A, 67(2):472-478 (2007).

Kawthekar, R.B. and Kim, G, Enantioselective Synthesis of β-Blockers via Hydrolytic Kinetic Resolution of Terminal Oxiranes by Using Bimetallic Chiral {{2,2'-[Cyclohexane-1,2-diylbis(nitrilomethylidyne)]bis[phenolato]}(2-)}cobalt ([Co(salen)]-Type Complexes, Helvetica Chimica Acta, 91:317-332 (2008).

Koike, Y. et al., N,N'-Bis(3-Cyclohexyl-5-Methylsalicylidene)-Alkylenediamines and their Metal Complexes, Kyushu University, 6(1):5-8 (1996).

(56) References Cited

OTHER PUBLICATIONS

Li, G. et al., Enantioselective Intramolecular Cyclopropanation of cis-Alkenes by Chiral Ruthenium(II) Schiff base Catalysts and Crystal Structures of (Schiff base)ruthenium Complexes Containing Carbene, PPh3, and CO Ligands, Organometallics, 25:1676-1688 (2006).

Lu, X. et al., Catalytic formation of ethylene carbonate from supercritical carbon dioxide/ethylene oxide mixture with tetradentate Schiff-base complexes as catalyst, Applied Catalysts A: General, 234(1-2):25-33 (2002).

Lu, X. et al., Synthesis, characterization and catalytic property of tetradentate Schiff-base complexes for the epoxidation of styrene, Journal of Molecular Catalysis, 250(1-2):62-69 (2006).

Mazet, C. and Jacobsen, E.N., Dinuclear {(salen)Al} Complexes Display Expanded Scope in the Conjugate Cyanation of $\alpha,\beta$-Unsaturated Imides, Angewandte Chemie International Edition, 47(9):1762-1765 (2008).

Mellah, M. et al., Electropolymerized Cr-salen complexes for the heterogeneous asymmetric hetero Diels-Alder reaction, Journal of Molecular Catalysis, 272(1-2):20-25 (2007).

Miller, J.A. et al., Axial Ligand Effects: Utilization of Chiral Sulf-oxide Additives for the Induction of Asymmetry in (Salen)ruthenium(II) Olefin Cyclopropanation Catalysts, Angewandte Chemie International Edition, 44:3885-3889 (2005).

Mitra, A. et al., Five-Coordinate Aluminum Bromides: Synthesis, Structure, Cation Formation, and Cleavage of Phosphate Ester Bonds, Journal of the American Chemical Society, 28(4):1147-1153 (2006).

Moore, D.R. et al., Electronic and Steric Effects on Catalysts for $CO_2$/Epoxide Polymerization: Subtle Modifications Resulting in Superior Activities, Angewandte Chemie International Edition, 41(14):2599-2602 (2002).

Nakano, K. et al., Selective Formation of Polycarbonate over Cyclic Carbonate: Copolymerization of Epoxides with Carbon Dioxide Catalyzed by a Cobalt(III) Complex with a Piperidinium End-Capping Arm, Angewandte Chemie International Edition, 45:7274-7277 (2006).

Noh, E.K. et al., Two Components in a Molecule: High Efficient and Thermally Robust Catalytic System for $CO_2$/Epoxide Copolymerization, Journal of the American Chemical Society, 129:8082-8083 (2007).

Qin, Z. et al., Cobalt-Based Complexes for the Copolymerization of Propylene Oxide and CO2: Active and Selective Catalysts for Polycarbonate Synthesis, Angewandte Chemie International Edition, 42:5484-5487 (2003).

Renehan, M.F. et al., Unsymmetrical chiral salen Schiff base ligands Synthesis and use in metal-based asymmetric expoxidation reactions, Journal of Molecular Catalysts. A: Chemica, 231(1-2): 205-220 (2005).

Schneider, H. and Hoppen, V. et al., Carbon-13 Nuclear Magnetic Resonance Substituent-Induced Shieldings and Conformational Equilibria in Cyclohexanes, Journal of Organic Chemistry, 43(20):3866-3873 (1978).

Shigeki, H, et al., Asymmetric oxidative coupling polymerization of dihydroxynaphtalene derivatives with cobalt-salen complexes, Polymer Bulletin, 59(3):303-310 (2007).

Shitama, H. et al., Synthesis of Metal-(Pentadentate-Salen) Complexes: Asymmetric Epoxidation with Aqueous Hydrogen Peroxide and Asymmetric Cyclopropanation (salen $H_2$: N,N'-bis-(salicylidene)ethylene-1,2-diamine), Chemistry: A European Journal, 13(17), 4849-4858 (2007).

Sugimoto, H. and Inoue, S., Recent progress in the synthesis of polymers based on carbon dioxide, Pure and Applied Chemistry, 78(10):1823-1834 (2006).

Sun, S. et al., Directed Assembly of Transition-Metal-Coordinated Molecular Loops and Squares from Salen-Type Components. Examples of Metalation-Controlled Structural Conversion, Journal of the American Chemical Society, 126(20):6314-6326 (2004).

Super, M.S. and Beckman, E.J., Copolymerizations Involving Carbon Dioxide: the Use of $CO_2$ as a Monomer, Trends in Polymer Science, 5:236-240 (1997).

Taylor, T.D. et al., First examples of the catalytic asymmetric ring-opening of meso 1,2-dioxines utlising cobalt$_{(II)}$ complexes with optically active tetradentate Schiff base ligands: formation of enantio-enriched cyclopropanes, Chemical Communications, 1:28-29 (2002).

Whitley, D.C., Van der Waals surface graphs and molecular shape, Journal of Mathematical Chemistry, 23:377-397 (1998).

Written Opinion for PCT/US2009/042926, 11 pages (dated Jul. 24, 2009).

Xu, X. et al., Effects of imidazolium salts as cocatalysts on the copolymerization of CO2 with epoxides catalyzed by (salen) CRIIICl complex, Polymer, 48(14):3921-3924 (2007).

COPOLYMERIZATION OF ETHYLENE OXIDE AND CARBON DIOXIDE

PRIORITY CLAIM

This application is a continuation of U.S. application Ser. No. 13/915,320, filed Jun. 11, 2013 now ABN, which is a continuation of U.S. application Ser. No. 12/990,202, filed Dec. 17, 2010 now ABN, which is a United States National Stage entry of International Application Number PCT/US09/42926, filed May 6, 2009, which claims priority to U.S. Provisional Patent Application Ser. No. 61/052,061, filed May 9, 2008, the entire contents of each of which is incorporated herein by reference.

BACKGROUND

Poly(ethylene carbonate) (PEC) is a flexible, biocompatible, and biodegradable material with high gas barrier properties, particularly for $O_2$. It is made via the ring opening polymerization of ethylene carbonate (EC) or by the copolymerization of ethylene oxide (EO) and $CO_2$. Ring opening polymerization of EC initiated by KOH or $Sn(OAc)_2$ at high temperature leads to poly(ethylene oxide-co-ether carbonate) rather than PEC. The high reaction temperatures required for this route cause the elimination of $CO_2$ during polymerization. The alternating copolymerization of epoxides and $CO_2$ to form polycarbonates was originally discovered by Inoue in 1969. Since then, numerous catalyst systems have been developed for epoxide/$CO_2$ copolymerization (see, for example, Coates and Moore, *Angew. Chem. Int. Ed.* 2004, 43, 6618-6639; Super and Beckman, *Trends Polym. Sci.* 1997, 5, 236-240; Darensbourg, and Holtcamp, *Coord. Chem. Rev.* 1996, 153, 155-174). Various systems for EO/$CO_2$ copolymerization based on Zn, Al, or double metal cyanide species have been reported; however, they require high $CO_2$ pressure and suffer from low catalytic activities.

SUMMARY

The present disclosure provides, in part, methods of synthesizing poly(ethylene carbonate) polymers from the reaction of ethylene oxide (EO) and carbon dioxide ($CO_2$) in the presence of a metal complex. The present disclosure also provides novel metal complexes. In particular, the inventors have found that N,N'-bis(salicydene)-1,2-cyclohexyldiamine (salcy) metal complexes are effective in this polymerization reaction, and particularly in providing poly(ethylene carbonate) polymers with low ether content.

In one aspect, the metal complexes as described herein are of the formula (I):

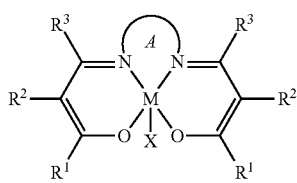

wherein:
M is a metal selected from zinc, cobalt, chromium, aluminum, titanium, ruthenium or manganese;
X is absent or is a nucleophilic ligand;

each instance of $R^1$, $R^2$, and $R^3$ is, independently, selected from hydrogen, halogen, optionally substituted aliphatic, optionally substituted heteroaliphatic, optionally substituted aryl, and optionally substituted heteroaryl, or $R^1$ and $R^2$, or $R^2$ and $R^3$, are joined to form an optionally substituted aryl or optionally substituted heteroaryl ring; and
Ring A forms an optionally substituted 5- to 6-membered ring.

In another aspect, the present disclosure provides a method of synthesizing a poly(ethylene carbonate) polymer, wherein the polymer is made up of Y, and optionally Z, and wherein the percentage of Y is greater than the percentage of Z,

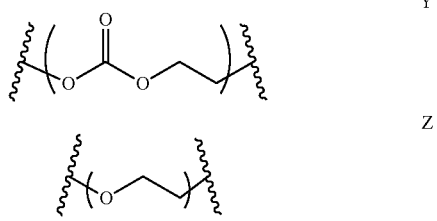

the method comprising reacting ethylene oxide and carbon dioxide in the presence of a metal complex.

In certain embodiments, the above method comprises a metal complex of formula (I), as described above and herein.

This application refers to various issued patent, published patent applications, journal articles, and other publications, all of which are incorporated herein by reference.

The details of one or more embodiments are set forth herein.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present disclosure can comprise one or more asymmetric centers, and thus can exist in various isomeric forms, e.g., stereoisomers and/or diastereomers. Thus, inventive compounds and compositions thereof may be in the form of an individual enantiomer, diastereomer or geometric isomer, or may be in the form of a mixture of stereoisomers. In certain embodiments, the compounds of the disclosure are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated.

The disclosure additionally encompasses the compounds as individual isomers substantially free of other isomers and alternatively, as mixtures of various isomers, e.g., racemic mixtures of stereoisomers. In addition to the above-mentioned compounds per se, this disclosure also encompasses pharmaceutically acceptable derivatives of these compounds and compositions comprising one or more compounds.

Where a particular enantiomer is preferred, it may, in some embodiments be provided substantially free of the opposite enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or bicyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present disclosure, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R$; —C(S)R°; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —C(S)NR°_2; —C(S)SR°; —SC(S)SR°, —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —N(OR°)R°; —C(NH)NR°_2; —P(O)_2R; —P(O)R°_2; —OP(O)R°_2; —OP(O)(OR°)_2; SiR_3; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —O(haloR$^●$), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-4}C(O)N(R°)_2$; —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —SiR$^●_3$, —OSiR$^●_3$, —C(O)SR$^●$, —$(C_{1-4}$ straight or branched alkylene)C(O)OR$^●$, or —SSR$^●$ wherein each $R^●$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_1$-6 aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three $R^\dagger$ substituents to provide a charged ammonium moiety $-N^+(R^\dagger)_3$, wherein the ammonium moiety is further complexed with a suitable counterion.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the disclosure. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present disclosure is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

As used herein, "polymorph" refers to a crystalline inventive compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

DETAILED DESCRIPTION OF CERTAIN EMBODIMENTS

Figure 1A:
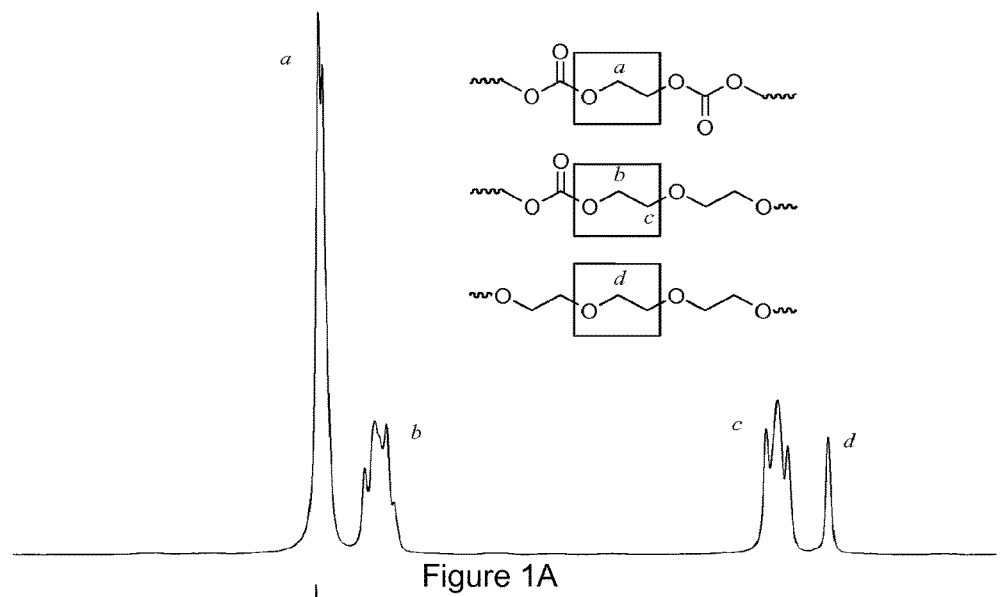
FIG. 1A. $^1$H NMR spectra (300 MHz) of PEC obtained by catalyst 1 in conjunction with [PPN]Cl.

As generally described above, the present disclosure provides methods of synthesizing poly(ethylene carbonate) compositions from ethylene oxide and carbon dioxide in the presence of a metal complex. In certain embodiments, the poly(ethylene carbonate) polymer is an alternating polymer. In certain embodiments, the poly(ethylene carbonate) polymer is a tapered co-polymer of polyethylene oxide and polyethylene carbonate. In certain embodiments, the poly (ethylene carbonate) polymer is a block co-polymer of polyethylene oxide and polyethylene carbonate.

As is generally understood from the description as provided herein, poly(ethylene carbonate) polymers of the present disclosure encompass poly(ethylene carbonate)

(PEC), as well as polymers which comprise poly(ethylene carbonate), such as, for example, polyethylene oxide-co-polyethylene carbonate.

The present disclosure also provides novel metal complexes of the formula (I) as is described in detail below.

I. Metal Complexes

In certain embodiments, the metal complex is of the formula (I):

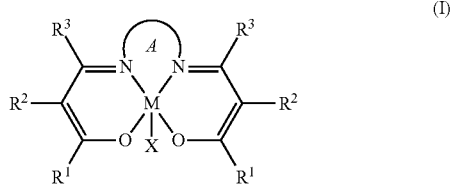

wherein:

M is a metal selected from zinc, cobalt, chromium, aluminum, titanium, ruthenium and manganese;

X is absent or is a nucleophilic ligand;

each instance of $R^1$, $R^2$, and $R^3$ is, independently, selected from hydrogen, halogen, optionally substituted aliphatic, optionally substituted heteroaliphatic, optionally substituted aryl, and optionally substituted heteroaryl, or $R^1$ and $R^2$, or $R^2$ and $R^3$, are joined to form an optionally substituted aryl or optionally substituted heteroaryl ring; and Ring A forms an optionally substituted 5- to 6-membered ring.

In certain embodiments, the metal is aluminum. In certain embodiments, the metal is chromium. In certain embodiments, the metal is zinc. In certain embodiments, the metal is titanium. In certain embodiments, the metal is ruthenium. In certain embodiments, the metal is manganese. In certain embodiments, the metal is cobalt. In certain embodiments, wherein the metal is cobalt, the cobalt has a valency of +3 (i.e., Co(III)).

In certain embodiments, the metal complex is a metal catalyst.

In certain embodiments, X is absent. However, in certain embodiments, X is a nucleophilic ligand. Exemplary nucleophilic ligands include, but are not limited to, —OR$^x$, —SR$^x$, —O(C=O)R$^x$, —O(C=O)OR$^x$, —O(C=O)N(R)$_2$, —N(R$^x$)(C=O)R$^x$, —NC, —CN, halo (e.g., —Br, —I, —Cl), —N$_3$, —O(SO$_2$)R$^x$ and —OPR$^x_3$, wherein each R$^x$ is, independently, selected from hydrogen, optionally substituted aliphatic, optionally substituted heteroaliphatic, optionally substituted aryl and optionally substituted heteroaryl.

In certain embodiments, X is —O(C=O)R$^x$, wherein R$^x$ is selected from optionally substituted aliphatic, fluorinated aliphatic, optionally substituted heteroaliphatic, optionally substituted aryl, fluorinated aryl, and optionally substituted heteroaryl.

For example, in certain embodiments, X is —O(C=O)R$^x$, wherein R$^x$ is optionally substituted aliphatic. In certain embodiments, X is —O(C=O)R$^x$, wherein R$^x$ is optionally substituted alkyl and fluoroalkyl. In certain embodiments, X is —O(C=O)CH$_3$ or —O(C=O)CF$_3$.

Furthermore, in certain embodiments, X is —O(C=O)R$^x$, wherein R$^x$ is optionally substituted aryl, fluoroaryl, or heteroaryl. In certain embodiments, X is —O(C=O)R$^x$, wherein R$^x$ is optionally substituted aryl. In certain embodiments, X is —O(C=O)R$^x$, wherein R$^x$ is optionally substituted phenyl. In certain embodiments, X is —O(C=O)C$_6$H$_5$ or —O(C=O)C$_6$F$_5$.

In certain embodiments, X is —OR$^x$, wherein R$^x$ is selected from optionally substituted aliphatic, optionally substituted heteroaliphatic, optionally substituted aryl, and optionally substituted heteroaryl.

For example, in certain embodiments, X is —OR$^x$, wherein R$^x$ is optionally substituted aryl. In certain embodiments, X is —OR$^x$, wherein R$^x$ is optionally substituted phenyl. In certain embodiments, X is —OC$_6$H$_5$ or —OC$_6$H$_2$(2,4-NO$_2$).

In certain embodiments, X is halo. In certain embodiments, X is —Br. In certain embodiments, X is —Cl. In certain embodiments, X is —I.

In certain embodiments, X is —O(SO$_2$)R$^x$. In certain embodiments X is —OTs. In certain embodiments X is —OSO$_2$Me, In certain embodiments X is —OSO$_2$CF$_3$.

In certain embodiments, X is —N$_3$.
In certain embodiments, X is —NC
In certain embodiments, X is —CN.

In certain embodiments, Ring A forms an optionally substituted 5-membered ring. In certain embodiments, Ring A forms an optionally substituted cyclopentyl ring. In certain embodiments, Ring A forms an optionally substituted 5-membered aryl ring.

In certain embodiments, Ring A forms an optionally substituted 6-membered ring. In certain embodiments, Ring A forms an optionally substituted cyclohexyl ring. In certain embodiments, Ring A forms an optionally substituted 6-membered aryl ring.

II. Northern and Southern Hemisphere of the Metal Complex

The metal complex of formula (I) may be considered in two portions: a Northern Hemisphere comprising the imine nitrogen atoms and Ring A, and Southern Hemisphere, comprising the rest of the metal complex.

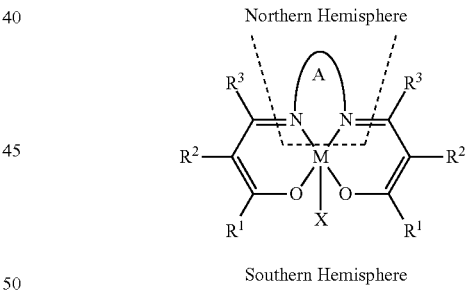

Northern Hemisphere

As generally understood from the above, the Northern Hemisphere of the metal complex is of the formula (i-a):

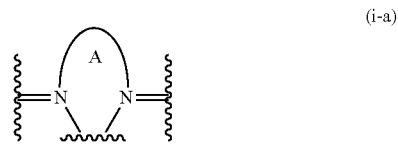

wherein Ring A forms an optionally substituted 5- to 6-membered ring.

In certain embodiments, Ring A forms an optionally substituted 6-membered ring of the formula (i-b):

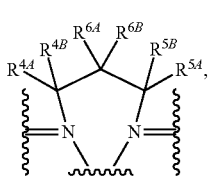

(i-b)

wherein $R^{4A}$, $R^{4B}$, $R^{5A}$, $R^{5B}$, and $R^{6A}$, $R^{6B}$ are, independently, selected from hydrogen, halogen, optionally substituted aliphatic, optionally substituted heteroaliphatic, optionally substituted aryl, optionally substituted heteroaryl, and/or, $R^{4A}$ and $R^{4B}$, and/or $R^{5A}$ and $R^{5B}$, and/or and $R^{6A}$ and $R^{6B}$ are optionally joined to form an oxo (=O) group, an oxime (=NOR$^a$) group, an imine (=NN(R$^a$)$_2$) group, an alkenyl (=C(R$^b$)$_2$) group, and/or a 3- to 6-membered spirocyclic ring, wherein each instance of R$^a$ and R$^b$ is, independently, hydrogen or optionally substituted aliphatic, wherein optionally two R$^a$ groups or two R$^b$ groups are joined to form a 3- to 6-membered ring.

In certain embodiments, $R^{4A}$, $R^{4B}$, $R^{5A}$, $R^{5B}$, $R^{6A}$, and $R^{6B}$ are, independently, selected from hydrogen, optionally substituted aliphatic, optionally substituted heteroaliphatic, optionally substituted aryl, and optionally substituted heteroaryl. In certain embodiments, $R^{4A}$, $R^{4B}$, $R^{5A}$, $R^{5B}$, $R^{6A}$, and $R^{6B}$ are, independently, selected from hydrogen and optionally substituted aliphatic. In certain embodiments, $R^{4A}$, $R^{4B}$, $R^{5A}$, $R^{5B}$, $R^{6A}$, and $R^{6B}$ are, independently, selected from hydrogen and optionally substituted heteroaliphatic. In certain embodiments, $R^{4A}$, $R^{4B}$, $R^{5A}$, $R^{5B}$, $R^{6A}$, and $R^{6B}$ are, independently, selected from hydrogen and optionally substituted aryl. In certain embodiments, $R^{4A}$, $R^{4B}$, $R^{5A}$, $R^{5B}$, $R^{6A}$, and $R^{6B}$ are, independently, selected from hydrogen and optionally substituted heteroaryl. In certain embodiments, two or more of $R^{4A}$, $R^{4B}$, $R^{5A}$, $R^{5B}$, $R^{6A}$, and $R^{6B}$, are joined to form one or more aliphatic, heteroaliphatic, aromatic, or heteroaromatic rings having 3 to 8 total ring atoms.

In certain embodiments, each of $R^{4A}$, $R^{4B}$, $R^{5A}$, $R^{5B}$, $R^{6A}$, and $R^{6B}$ are hydrogen.

For example, in certain embodiments of formula (i-b), wherein each of $R^{4A}$, $R^{4B}$, $R^{5A}$, $R^{5B}$, $R^{6A}$, and $R^{6B}$ are hydrogen, Ring A forms a 6-membered ring of the formula:

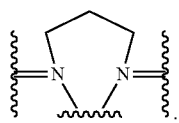

In certain embodiments, Ring A forms an optionally substituted 6-membered ring of the formula (i-c):

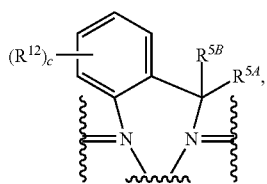

(i-c)

wherein $R^{5A}$ and $R^{5B}$ are, independently, selected from hydrogen, halogen, optionally substituted aliphatic, optionally substituted heteroaliphatic, optionally substituted aryl, optionally substituted heteroaryl, and/or, $R^{5A}$ and $R^{5B}$ are optionally joined to form an oxo (=O) group, an oxime (=NOR$^a$) group, an imine (=NN(R$^a$)$_2$) group, an alkenyl (=C(R$^b$)$_2$) group, and/or a 3- to 6-membered spirocyclic ring, wherein each instance of R$^a$ and R$^b$ is, independently, hydrogen or optionally substituted aliphatic, wherein optionally two R$^a$ groups or two R$^b$ groups are joined to form a 5- to 6-membered ring;

each instance of $R^{12}$ is selected from hydrogen, halogen, —OR$^c$, —OC(=O)R$^c$, —OC(=O)OR$^c$, —OC(=O)N(R$^d$)$_2$, —OSO$_2$R$^d$, —C(=O)OR$^c$, —C(=O)N(R$^d$)$_2$, —CN, —CNO, —NCO, —N$_3$, —NO2, —N(R$^d$)$_2$, —N(R$^d$)C(=O)R$^c$, —N(R$^d$)C(=O)OR$^c$, —N(R$^d$)SO$_2$R$^d$, —SO$_2$R$^d$, —SOR$^d$, —SO$_2$N(R$^d$)$_2$, optionally substituted aliphatic, optionally substituted heteroaliphatic, optionally substituted aryl, optionally substituted heteroaryl, wherein each instance of R$^c$ is, independently, optionally substituted aliphatic, optionally substituted heteroaliphatic, optionally substituted aryl, optionally substituted heteroaryl, and each instance of R$^d$ is, independently, hydrogen, optionally substituted aliphatic, optionally substituted heteroaliphatic, optionally substituted aryl, optionally substituted heteroaryl; and c is 0 to 4.

In certain embodiments, $R^{5A}$ and $R^{5B}$ are, independently, selected from hydrogen and optionally substituted aliphatic. In certain embodiments, $R^{5A}$ and $R^{5B}$ are, independently, selected from hydrogen and optionally substituted heteroaliphatic. In certain embodiments, $R^{5A}$ and $R^{5B}$ are, independently, selected from hydrogen and optionally substituted aryl. In certain embodiments, $R^{5A}$ and $R^{5B}$ are, independently, selected from hydrogen and optionally substituted heteroaryl.

However, in certain embodiments, each $R^{5A}$ and $R^{5B}$ is hydrogen.

In certain embodiments, c is 0 to 2. In certain embodiments, c is 0 to 1. In certain embodiments, c is 0. In certain embodiments, c is 1.

In certain embodiments, each instance of $R^{12}$ is, independently, selected from hydrogen and optionally substituted aliphatic. In certain embodiments, each instance of $R^{12}$ is, independently, selected from hydrogen and optionally substituted heteroaliphatic. In certain embodiments, each instance of $R^{12}$ is, independently, selected from hydrogen and optionally substituted aryl. In certain embodiments, each instance of $R^{12}$ is, independently, selected from hydrogen and optionally substituted heteroaryl.

However, in certain embodiments, each instance of $R^{12}$ is hydrogen.

In certain embodiments, Ring A forms an optionally substituted 5-membered ring of the formula (i-d):

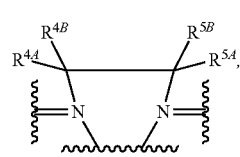

(i-d)

wherein $R^{4A}$, $R^{4B}$, $R^{5A}$, and $R^{5B}$ are, independently, selected from hydrogen, halogen, optionally substituted aliphatic, optionally substituted heteroaliphatic, optionally substituted aryl, optionally substituted heteroaryl, and/or, $R^{4A}$ and $R^{4B}$ and/or $R^{5A}$ and $R^{5B}$ are optionally joined to form an oxo (=O) group, an oxime (=NOR$^a$) group, an imine (=NN(R$^a$)$_2$) group, an alkenyl (=C(R$^b$)$_2$) group, and/or a 3- to 6-membered spirocyclic ring, wherein each instance of R$^a$ and R$^b$ is, independently, hydrogen or optionally substituted aliphatic, wherein optionally two R$^a$ groups or two R$^b$ groups are joined to form a 5- to 6-membered ring.

In certain embodiments, wherein $R^{4A}$, $R^{4B}$, $R^{5A}$, and $R^{5B}$ are, independently, selected from hydrogen, optionally substituted aliphatic, optionally substituted heteroaliphatic, optionally substituted aryl, optionally substituted heteroaryl, or wherein one of $R^{4A}$, $R^{4B}$, $R^{5A}$, and $R^{5B}$ and one of $R^{4A}$, $R^{4B}$, $R^{5A}$, and $R^{5B}$ are optionally joined to form a 3- to 7-membered ring.

In certain embodiments, $R^{4A}$, $R^{4B}$, $R^{5A}$, and $R^{5B}$ are, independently, selected from hydrogen and optionally substituted aliphatic. In certain embodiments, $R^{4A}$, $R^{4B}$, $R^{5A}$, and $R^{5B}$ are, independently, selected from hydrogen and optionally substituted heteroaliphatic. In certain embodiments, $R^{4A}$, $R^{4B}$, $R^{5A}$, and $R^{5B}$ are, independently, selected from hydrogen and optionally substituted aryl. In certain embodiments, $R^{4A}$, $R^{4B}$, $R^{5A}$, and $R^{5B}$ are, independently, selected from hydrogen and optionally substituted heteroaryl. In certain embodiments, one of $R^{4A}$, $R^{4B}$, $R^{5A}$, and $R^{5B}$ and one of $R^{4A}$, $R^{4B}$, $R^{5A}$, and $R^{5B}$ are optionally joined to form a 3- to 6-membered ring.

However, in certain embodiments, each instance of $R^{4A}$, $R^{4B}$, $R^{5A}$, and $R^{5B}$ is hydrogen.

For example, in certain embodiments of formula (i-d), wherein $R^{4A}$, $R^{4B}$, $R^{5A}$, and $R^{5B}$ are each hydrogen, Ring A forms a 5-membered ring of the formula:

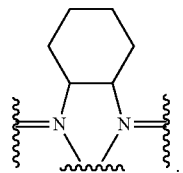

(i-e)

In certain embodiments of formula (i-d), wherein $R^{4B}$ and $R^{5B}$ are joined to form an optionally substituted 6-membered ring, Ring A forms an optionally substituted 5-membered ring of the formula (i-f):

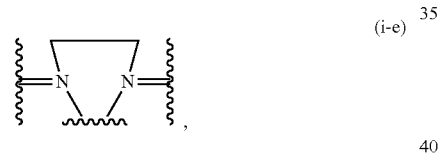

(i-f)

wherein $R^{4A}$, $R^{5A}$, $R^{13A}$, $R^{13B}$, $R^{14A}$, $R^{14B}$, $R^{5A}$, $R^{15B}$, $R^{16A}$, $R^{16B}$ are, independently, selected from hydrogen, halogen, —OR$^c$, —OC(=O)R$^c$, —OC(=O)OR$^c$, —OC(=O)N(R$^d$)$_2$, —OSO$_2$R$^d$, —C(=O)R$^c$, —C(=O)N(R$^d$)$_2$, —CN, —CNO, —NCO, —N$_3$, —NO2, —N(R$^d$)$_2$, —N(R$^d$)C(=O)OR$^c$, —N(R$^d$)C(=O)R$^c$, —N(R$^d$)SO$_2$R$^d$, —SO$_2$R$^d$, —SOR$^d$, —SO$_2$N(R$^d$)$_2$, optionally substituted aliphatic, optionally substituted heteroaliphatic, optionally substituted aryl, optionally substituted heteroaryl; and/or, optionally, $R^{13A}$ and $R^{13B}$, and/or $R^{14A}$ and $R^{14B}$, and/or $R^{15A}$ and $R^{15B}$, and/or $R^{16A}$ and $R^{16B}$ are optionally joined to form an oxo (=O) group, an oxime (=NOR$^a$) group, an imine (=NN(R$^a$)$_2$) group, an alkenyl (=C(R$^b$)$_2$) group, and/or a 3- to 6-membered spirocyclic ring, wherein each instance of R$^a$ and R$^b$ is, independently, hydrogen or optionally substituted aliphatic, wherein optionally two R$^a$ groups or two R$^b$ groups are joined to form a 3- to 6-membered ring.

In certain embodiments, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are, independently, selected from hydrogen, halogen, optionally substituted aliphatic, optionally substituted heteroaliphatic, optionally substituted aryl, optionally substituted heteroaryl. In certain embodiments, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are, independently, selected from hydrogen and optionally substituted aliphatic. In certain embodiments, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are, independently, selected from hydrogen and optionally substituted heteroaliphatic. In certain embodiments, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are, independently, selected from hydrogen and optionally substituted aryl. In certain embodiments, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are, independently, selected from hydrogen and optionally substituted heteroaryl.

However, in certain embodiments, each of $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ is hydrogen.

For example, in certain embodiments of formula (i-d), wherein $R^{4B}$ and $R^{5B}$ are joined to form an optionally substituted 6-membered ring and each of $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ is hydrogen, Ring A forms an optionally substituted 5-membered ring of the formula (i-g):

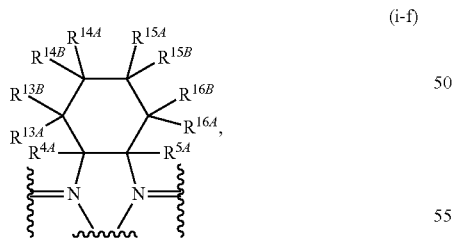

(i-g)

In certain embodiments of formula (i-d), wherein $R^{4B}$ and $R^{5B}$ are joined to form an optionally substituted 6-membered ring, Ring A forms an optionally substituted 5-membered ring of any of the formulae (i-h) to (i-k):

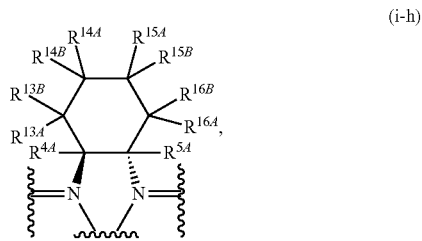

(i-h)

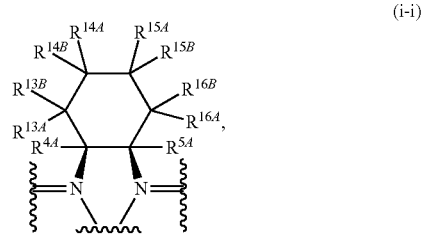

(i-i)

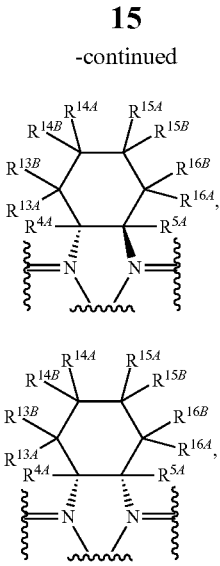

or a mixture thereof;

wherein $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are, independently, selected from hydrogen, halogen, —$OR^c$, —$OC(=O)R^c$, —$OC(=O)OR^c$, $OC(=O)N(R^d)_2$, —$OSO_2R^d$, —$C(=O)OR^c$, —$C(=O)N(R^d)_2$, —CN, —CNO, —NCO, —$N_3$, —NO2, —$N(R^d)_2$, —$N(R^d)C(=O)OR^c$, —$N(R^d)C(=O)R^c$, —$N(R^d)SO_2R^d$, —$SO_2R^d$, —$SOR^d$, —$SO_2N(R^d)_2$, optionally substituted aliphatic, optionally substituted heteroaliphatic, optionally substituted aryl, optionally substituted heteroaryl, and/or, $R^{13A}$ and $R^{13B}$, and/or $R^{14A}$ and $R^{14B}$, and/or $R^{15A}$ and $R^{15B}$, and/or $R^{16A}$ and $R^{16B}$ are optionally joined to form an oxo (=O) group, an oxime (=$NOR^a$) group, an imine (=$NN(R^a)_2$) group, an alkenyl (=$C(R^b)_2$) group, and/or a 3- to 6-membered spirocyclic ring, wherein each instance of $R^a$ and $R^b$ is, independently, hydrogen or optionally substituted aliphatic, wherein optionally two $R^a$ groups or two $R^b$ groups are joined to form a 5- to 6-membered ring.

In certain embodiments of formulae (i-h) to (i-k), wherein $R^{4B}$ and $R^{5B}$ are joined to form an optionally substituted 6-membered ring, and $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are each hydrogen, Ring A forms an optionally substituted 5-membered ring of any of the formulae (i-l) to (i-o):

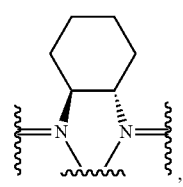

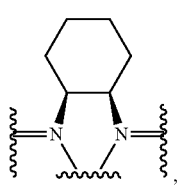

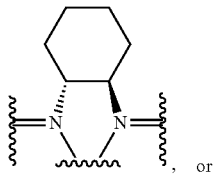

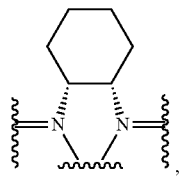

or any mixture thereof.

In certain embodiments of formula (i-d), wherein $R^{4B}$ and $R^{5B}$ are joined to form an optionally substituted 6-membered ring, Ring A forms an optionally substituted 5-membered ring of the formula (i-p):

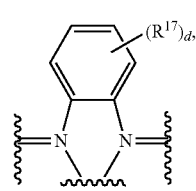

wherein each instance of $R^{17}$ is, independently, selected from hydrogen, halogen, —$OR^c$, —$OC(=O)R^c$, —$OC(=O)OR^c$, —$OC(=O)N(R^d)_2$, —$OSO_2R^d$, —$C(=O)OR^c$, —$C(=O)N(R^d)_2$, —CN, —CNO, —NCO, —$N_3$, —$NO_2$, —$N(R^d)_2$, —$N(R^d)C(=O)OR^c$, —$N(R^d)C(=O)R^c$, —$N(R^d)SO_2R^d$, —$SO_2R^d$, —$SOR^d$, —$SO_2N(R^d)_2$, optionally substituted aliphatic, optionally substituted heteroaliphatic, optionally substituted aryl, optionally substituted heteroaryl, wherein each instance of $R^c$ is, independently, optionally substituted aliphatic, optionally substituted heteroaliphatic, optionally substituted aryl, optionally substituted heteroaryl, and each instance of $R^d$ is, independently, hydrogen, optionally substituted aliphatic, optionally substituted heteroaliphatic, optionally substituted aryl, optionally substituted heteroaryl; and/or two $R^{17}$ groups adjacent to each other are joined to form an optionally substituted 5- to 6-membered ring; and d is 0 to 4.

In certain embodiments, d is 0 to 2. In certain embodiments, d is 0 to 1. In certain embodiments, d is 0. In certain embodiments, d is 1.

In certain embodiments, each instance of $R^{17}$ is, independently, selected from hydrogen, optionally substituted aliphatic, optionally substituted heteroaliphatic, optionally substituted aryl, and optionally substituted heteroaryl. In certain embodiments, each instance of $R^{17}$ is, independently, selected from hydrogen and optionally substituted aliphatic. In certain embodiments, each instance of $R^{17}$ is, independently, selected from hydrogen and optionally substituted heteroaliphatic. In certain embodiments, each instance of $R^{17}$ is, independently, selected from hydrogen and optionally substituted aryl. In certain embodiments, each instance of $R^{17}$ is, independently, selected from hydrogen and optionally substituted heteroaryl.

However, in certain embodiments, each instance of $R^{17}$ is hydrogen.

For example, in certain embodiments of formula (i-p), wherein $R^{4B}$ and $R^{5B}$ are joined to form an optionally substituted 6-membered ring, Ring A forms an optionally substituted 5-membered ring of the formula (i-q):

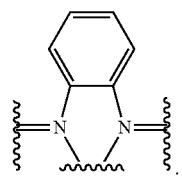

(i-q)

Southern Hemisphere

As generally understood from the above, the Southern Hemisphere of the metal complex is of the formula (ii-a):

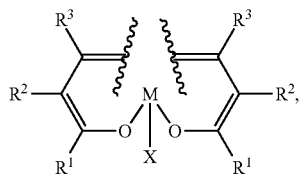

(ii-a)

wherein M and X are as defined above and herein, and each instance of $R^1$, $R^2$, and $R^3$ is, independently, selected from hydrogen, halogen, —$OR^c$, —$OC(=O)R^c$, —$OC(=O)OR^c$, —$OC(=O)N(R^d)_2$, —$OSO_2R^d$, —$C(=O)OR^c$, —$C(=O)N(R^d)_2$, —CN, —CNO, —NCO, —$N_3$, —$NO_2$, —$N(R^d)_2$, —$N(R^d)C(=O)OR^c$, —$N(R^d)C(=O)R^c$, —$N(R^d)SO_2R^d$, —$SO_2R^d$, —$SOR^d$, —$SO_2N(R^d)_2$, optionally substituted aliphatic, optionally substituted heteroaliphatic, optionally substituted aryl, and optionally substituted heteroaryl, and/or any of $R^1$ and $R^2$, and/or any of $R^2$ and $R^3$, are joined to form an optionally substituted aryl or optionally substituted heteroaryl ring.

In certain embodiments, $R^1$ is hydrogen, halogen, optionally substituted aliphatic, optionally substituted heteroaliphatic, optionally substituted aryl, or optionally substituted heteroaryl. In certain embodiments, each instance of $R^1$ is hydrogen. In certain embodiments, each instance of $R^1$ is halogen. In certain embodiments, each instance of $R^1$ is optionally substituted aliphatic. In certain embodiments, each instance of $R^1$ is optionally substituted heteroaliphatic. In certain embodiments, each instance of $R^1$ is optionally substituted aryl. In certain embodiments, each instance of $R^1$ is optionally substituted heteroaryl.

In certain embodiments, each instance of $R^2$ is hydrogen, halogen, optionally substituted aliphatic, optionally substituted heteroaliphatic, optionally substituted aryl, or optionally substituted heteroaryl. In certain embodiments, each instance of $R^2$ is hydrogen. In certain embodiments, each instance of $R^2$ is halogen. In certain embodiments, each instance of $R^2$ is optionally substituted aliphatic. In certain embodiments, each instance of $R^2$ is optionally substituted heteroaliphatic. In certain embodiments, each instance of $R^2$ is optionally substituted aryl. In certain embodiments, each instance of $R^2$ is optionally substituted heteroaryl.

In certain embodiments, each instance of $R^3$ is hydrogen, halogen, optionally substituted aliphatic, optionally substituted heteroaliphatic, optionally substituted aryl, or optionally substituted heteroaryl. In certain embodiments, each instance of $R^3$ is hydrogen. In certain embodiments, each instance of $R^3$ is halogen. In certain embodiments, each instance of $R^3$ is optionally substituted aliphatic. In certain embodiments, each instance of $R^3$ is optionally substituted heteroaliphatic. In certain embodiments, each instance of $R^3$ is optionally substituted aryl. In certain embodiments, each instance of $R^3$ is optionally substituted heteroaryl.

However, in certain embodiments, $R^1$ and $R^2$ are joined to form an optionally substituted aryl or optionally substituted heteroaryl ring. In certain embodiments, $R^1$ and $R^2$ are joined to form an optionally substituted aryl ring. In certain embodiments, $R^1$ and $R^2$ are joined to form an optionally substituted heteroaryl ring.

In other embodiments, $R^2$ and $R^3$ are joined to form an optionally substituted aryl or optionally substituted heteroaryl ring. In certain embodiments, $R^2$ and $R^3$ are joined to form an optionally substituted aryl ring. In certain embodiments, $R^2$ and $R^3$ are joined to form an optionally substituted heteroaryl ring.

In certain embodiments, each instance of $R^1$, $R^2$, and $R^3$ is, independently, selected from hydrogen, optionally substituted aliphatic, and/or any of $R^1$ and $R^2$, and/or any of $R^2$ and $R^3$, are joined to form an optionally substituted aryl or optionally substituted heteroaryl ring. In certain embodiments, each instance of $R^1$, $R^2$, and $R^3$ is, independently, selected from hydrogen and/or any of $R^1$ and $R^2$ are joined to form an optionally substituted aryl or optionally substituted heteroaryl ring. In certain embodiments, each instance of $R^1$, $R^2$, and $R^3$ is, independently, selected from hydrogen and/or any of $R^2$ and $R^3$, are joined to form an optionally substituted aryl or optionally substituted heteroaryl ring.

In certain embodiments, each instance of $R^1$, $R^2$, and $R^3$ is, independently, selected from hydrogen and optionally substituted aliphatic. In certain embodiments, each instance of $R^1$, $R^2$, and $R^3$ is, independently, selected from hydrogen and optionally substituted heteroaliphatic. In certain embodiments, each instance of $R^1$, $R^2$, and $R^3$ is, independently, selected from hydrogen and optionally substituted aryl. In certain embodiments, each instance of $R^1$, $R^2$, and $R^3$ is, independently, selected from hydrogen and optionally substituted heteroaryl.

However, in certain embodiments, each instance of $R^1$, $R^2$, and $R^3$ is hydrogen. In certain embodiments, each instance of $R^1$ and $R^3$ is hydrogen. In certain embodiments, each instance of $R^2$ and $R^3$ is hydrogen. In certain embodiments, each instance of $R^1$ and $R^2$ is hydrogen. In certain embodiments, each instance of $R^1$ is hydrogen. In certain embodiments, each instance of $R^2$ is hydrogen. In certain embodiments, each instance of $R^3$ is hydrogen.

In certain embodiments, wherein $R^1$ is an optionally substituted aryl moiety, the Southern Hemisphere of the metal complex is of the formula (ii-b):

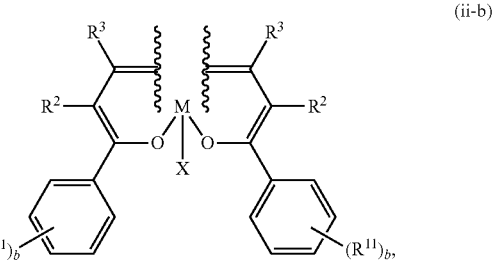

(ii-b)

wherein M, X, $R^2$ and $R^3$ are as defined above and herein;

each instance of $R^{11}$ is, independently, selected from hydrogen, halogen, —$OR^c$, —$OC(=O)R^c$, —$OC(=O)OR^c$, —$OC(=O)N(R^d)_2$, —$OSO_2R^d$, —$C(=O)OR^c$, —$C(=O)N(R^d)_2$, —CN, —CNO, —NCO, —$N_3$, —$NO_2$, —$N(R^d)_2$, —$N(R^d)C(=O)OR^c$, —$N(R^d)C(=O)R^c$, —$N(R^d)SO_2R^d$, —$SO_2R^d$, —$SOR^d$, —$SO_2N(R^d)_2$, optionally substituted aliphatic, optionally substituted heteroaliphatic, optionally substituted aryl, optionally substituted heteroaryl, wherein each instance of $R^c$ is, independently, optionally substituted aliphatic, optionally substituted heteroaliphatic, optionally substituted aryl, optionally substituted heteroaryl, and each instance of $R^d$ is, independently, hydrogen, optionally substituted aliphatic, optionally substituted heteroaliphatic, optionally substituted aryl, optionally substituted heteroaryl; and/or two $R^{11}$ groups adjacent to each other are joined to form an optionally substituted 5- to 6-membered ring; and b is 0 to 5.

In certain embodiments, b is 0 to 2. In certain embodiments, b is 0 to 1. In certain embodiments, b is 0. In certain embodiments, b is 1.

In certain embodiments, each instance of $R^{11}$ is, independently, selected from hydrogen, optionally substituted aliphatic, optionally substituted heteroaliphatic, optionally substituted aryl, and optionally substituted heteroaryl, and/or two $R^{11}$ groups adjacent to each other are joined to form an optionally substituted 5- to 6-membered ring. In certain embodiments, each instance of $R^{11}$ is, independently, selected from hydrogen and optionally substituted aliphatic. In certain embodiments, each instance of $R^{11}$ is, independently, selected from hydrogen, optionally substituted heteroaliphatic. In certain embodiments, each instance of R is, independently, selected from hydrogen, optionally substituted aryl. In certain embodiments, each instance of $R^{11}$ is, independently, selected from hydrogen, optionally substituted heteroaryl.

However, in certain embodiments, each instance of $R^{11}$ is hydrogen.

In certain embodiments, wherein one of $R^1$ and $R^2$ are joined to form an optionally substituted aryl ring, the Southern Hemisphere of the metal complex is of the formula (ii-c):

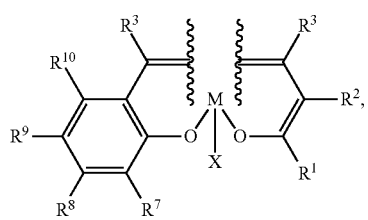

(ii-c)

wherein M, X, $R^1$, $R^2$ and $R^3$ are, as defined above and herein; and $R^7$, $R^8$, $R^9$, and $R^{10}$, are, independently, selected from hydrogen, halogen, —$OR^c$, —$OC(=O)R^c$, —$OC(=O)OR^c$, —$OC(=O)N(R^d)_2$, —$OSO_2R^d$, —$C(=O)OR^c$, —$C(=O)N(R^d)_2$, —CN, —CNO, —NCO, —$N_3$, —$NO_2$, —$N(R^d)_2$, —$N(R^d)C(=O)OR^c$, —$N(R^d)C(=O)R^c$, —$N(R^d)SO_2R^d$, —$SO_2R^d$, —$SOR^d$, —$SO_2N(R^d)_2$, optionally substituted aliphatic, optionally substituted heteroaliphatic, optionally substituted aryl, optionally substituted heteroaryl, wherein each instance of $R^c$ is, independently, optionally substituted aliphatic, optionally substituted heteroaliphatic, optionally substituted aryl, optionally substituted heteroaryl, and each instance of $R^d$ is, independently, hydrogen, optionally substituted aliphatic, optionally substituted heteroaliphatic, optionally substituted aryl, optionally substituted heteroaryl; and/or two groups selected from $R^7$, $R^8$, $R^9$, and $R^{10}$ adjacent to each other are joined to form an optionally substituted 5- to 6-membered ring.

In certain embodiments, $R^7$, $R^8$, $R^9$, and $R^{10}$ are, independently, selected from hydrogen, optionally substituted aliphatic, optionally substituted heteroaliphatic, optionally substituted aryl, and optionally substituted heteroaryl, and/or two groups selected from $R^7$, $R^8$, $R^9$, and $R^{10}$ adjacent to each other are joined to form an optionally substituted 5- to 7-membered ring. In certain embodiments, $R^7$, $R^8$, $R^9$, and $R^{10}$ are, independently, selected from hydrogen and optionally substituted aliphatic. In certain embodiments, $R^7$, $R^8$, $R^9$, and $R^{10}$ are, independently, selected from hydrogen and optionally substituted heteroaliphatic. In certain embodiments, $R^7$, $R^8$, $R^9$, and $R^{10}$ are, independently, selected from hydrogen and optionally substituted aryl. In certain embodiments, $R^7$, $R^8$, $R^9$, and $R^{10}$ are, independently, selected from hydrogen and optionally substituted heteroaryl.

In certain embodiments, $R^7$, $R^8$, $R^9$, and $R^{10}$ are, independently, selected from hydrogen and optionally substituted aryl. In certain embodiments, $R^7$, $R^8$, $R^9$, and $R^{10}$ are, independently, selected from hydrogen and optionally substituted phenyl.

In certain embodiments, $R^7$, $R^8$, $R^9$, and $R^{10}$ are, independently, selected from hydrogen and optionally substituted $C_{1-10}$ aliphatic. In certain embodiments, $R^7$, $R^8$, $R^9$, and $R^{10}$ are, independently, selected from hydrogen and optionally substituted $C_{1-10}$ alkyl. In certain embodiments, $R^7$, $R^8$, $R^9$, and $R^{10}$ are, independently, selected from hydrogen and methyl, trichloromethyl, trifluoromethyl, ethyl, n-propyl, isopropyl, t-butyl, sec-butyl, iso-butyl, n-pentyl, neopentyl, amyl, trityl, adamantyl, thexyl, benzyl and cumyl.

However, in certain embodiments, each of $R^7$, $R^8$, $R^9$, and $R^{10}$ are hydrogen. In certain embodiments, each of $R^8$ and $R^{10}$ are hydrogen. In certain embodiments, $R^8$ is hydrogen. In certain embodiments, $R^{10}$ is hydrogen.

For example, in certain embodiments of the formula (ii-c), wherein $R^8$ and $R^{10}$ are hydrogen, the Southern Hemisphere of the metal complex is of the formula (ii-d):

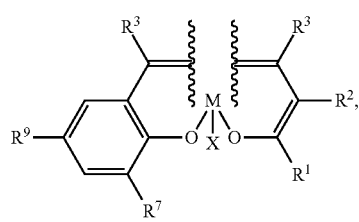

(ii-d)

wherein M, X, $R^1$, $R^2$, $R^3$, $R^7$ and $R^9$ are, as defined above and herein.

In certain embodiments, of the formula (ii-d), wherein both $R^1$ and $R^2$ groups are joined to form an optionally substituted aryl ring, the Southern Hemisphere of the metal complex is of the formula (ii-dd):

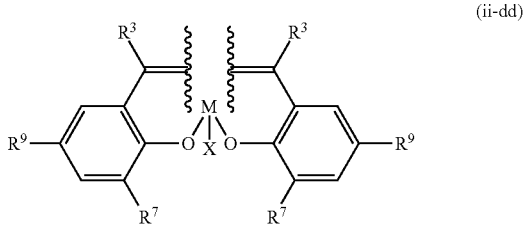

(ii-dd)

wherein M, X, $R^3$, $R^7$ and $R^9$ are, as defined above and herein.

In certain embodiments, each occurrence of $R^3$ is, independently, selected from hydrogen, halogen, optionally substituted aliphatic, optionally substituted heteroaliphatic, optionally substituted aryl, and optionally substituted heteroaryl. In certain embodiments, each occurrence of $R^3$ is hydrogen.

In certain embodiments, each occurrence of $R^7$ and $R^9$ is independently selected from hydrogen, optionally substituted aliphatic, optionally substituted heteroaliphatic, optionally substituted aryl, and optionally substituted heteroaryl.

In certain embodiments, each occurrence of $R^7$ and $R^9$ is independently selected from hydrogen, optionally substituted aliphatic and optionally substituted aryl.

In certain embodiments, each occurrence of $R^7$ is the same. In certain embodiments, each occurrence of $R^9$ is the same. In certain embodiments, each occurrence of $R^7$ is the same and each occurrence of $R^9$ is the same. In certain embodiments, $R^7$ and $R^9$ are different.

In certain embodiments, each occurrence of $R^7$ and $R^9$ is independently selected from hydrogen and optionally substituted $C_{1-12}$ aliphatic. In certain embodiments, each occurrence of $R^7$ and $R^9$ is independently selected from hydrogen and optionally substituted $C_{1-12}$ alkyl. In certain embodiments, each occurrence of $R^7$ and $R^9$ is independently selected from hydrogen, methyl, trichloromethyl, trifluoromethyl, ethyl, n-propyl, isopropyl, t-butyl, sec-butyl, isobutyl, n-pentyl, neopentyl, amyl, trityl, adamantyl, thexyl, benzyl and cumyl.

In some embodiments $R^7$ is hydrogen. In some embodiments $R^7$ is methyl. In some embodiments $R^7$ is trichloromethyl. In some embodiments $R^7$ is trifluoromethyl. In some embodiments $R^7$ is ethyl. In some embodiments $R^7$ is n-propyl. In some embodiments $R^7$ is isopropyl. In some embodiments $R^7$ is t-butyl. In some embodiments $R^7$ is sec-butyl. In some embodiments $R^7$ is iso-butyl. In some embodiments $R^7$ is n-pentyl. In some embodiments $R^7$ is neopentyl. In some embodiments $R^7$ is amyl. In some embodiments $R^7$ is trityl. In some embodiments $R^7$ is adamantyl. In some embodiments $R^7$ is thexyl. In some embodiments $R^7$ is benzyl. In some embodiments $R^7$ is cumyl.

In some embodiments $R^9$ is hydrogen. In some embodiments $R^9$ is methyl. In some embodiments $R^9$ is trichloromethyl. In some embodiments $R^9$ is trifluoromethyl. In some embodiments $R^9$ is ethyl. In some embodiments $R^9$ is n-propyl. In some embodiments $R^9$ is isopropyl. In some embodiments $R^9$ is t-butyl. In some embodiments $R^9$ is sec-butyl. In some embodiments $R^9$ is iso-butyl. In some embodiments $R^9$ is n-pentyl. In some embodiments $R^9$ is neopentyl. In some embodiments $R^9$ is amyl. In some embodiments $R^9$ is trityl. In some embodiments $R^9$ is adamantyl. In some embodiments $R^9$ is thexyl. In some embodiments $R^9$ is benzyl. In some embodiments $R^9$ is cumyl.

In certain embodiments, each occurrence of $R^7$ and $R^9$ is independently selected from hydrogen and optionally substituted aryl. In certain embodiments, each occurrence of $R^7$ and $R^9$ is independently selected from hydrogen and optionally substituted phenyl.

Without wishing to be bound by any theory, it is believed that the relative sizes of the $R^7$ and $R^9$ groups influence the rate and selectivity of the polymerization reactions catalyzed by the metal complexes In certain embodiments it is advantageous for there to be a difference in the sizes of $R^7$ and $R^9$. In certain embodiments, the group $R^7$ is larger than the group $R^9$. However, in certain embodiments, the group $R^9$ is larger than the group $R^7$.

The relative size of a group (e.g., in this instance, $R^7$ to $R^9$) can be determined from the van der Waals surface and/or molecular volume as calculated for that group. For a single molecule (i.e., a molecule for which there is a path between any two atoms along covalent bonds), the van der Waals surface is a closed surface, and hence, it contains volume. This volume is called the molecular volume, or van der Waals volume, and is usually given in $Å^3$. The straightforward way of calculating molecular volume on the computer is by numerical integration, i.e., by surrounding the van der Waals envelope with a grid of small bricks and summing up the bricks whose centers are within the van der Waals envelope of the molecule (i.e., are within a van der Waals radius from atom nucleus) (see, for example, Whitley, "Van der Waals surface graphs and molecular shape," *Journal of Mathematical Chemistry* (1998) 23:377-397).

The relative size of a group can also be measured from the "A-value" for a given group. The A-value is a measure of the effective size of a given group. The "A-value" refers to the conformational energies (-$G^0$ values) as determined for a substituted cyclohexane and the relative axial-equatorial disposition of the substituent (see Table 1, provided below, and pages 695-697 of Eliel and Wilen, Chapter 11 entitled "Configuration and Confirmation of Cyclic Molecules" of *Stereochemistry of Organic Compounds*, John Wiley & Sons, Inc., New York: 1994, incorporated herein by reference). More detailed tabulations have been compiled by Hirsch, "Table of Conformational Energies", *Top. Stereochem.* (1967) 1:199; Jensen and Bushweller, "Conformational Preferences in Cyclohexanes and Cyclohexenes", *Adv. Alicycl. Chem.* (1971) 3:139; and Schnieder and Hoppen "Carbon-13 Nuclear Magnetic Resonance Substituent-induced Shieldings and Conformational Equilibria in Cyclohexanes", *J. Org. Chem.* (1978) 43:3866; the entirety of each of which is incorporated herein by reference.

TABLE 1

Exemplary A-values

| Group | -$G^0$ value | |
|---|---|---|
| | kcal/mol | kJ/mol |
| —H | ~0 | ~0 |
| -D | 0.0006 | 0.025 |
| -T | 0.011 | 0.046 |
| —F | 0.25-0.42 | 1.05-1.75 |
| —Cl | 0.53-0.64 | 2.22-2.68 |
| —Br | 0.48-0.67 | 2.01-2.80 |
| —I | 0.47-0.61 | 1.97-2.55 |
| —OtBu | 0.75 | 3.14 |
| —OPh | 0.65 | 2.72 |
| —OC(=O)CH$_3$ | 0.68-0.87 | 2.85-3.64 |
| —OSi(CH$_3$)$_3$ | 0.74 | 3.10 |
| —NO$_2$ | 1.1 | 4.8 |
| —P(CH$_3$)$_2$ | 1.5-1.6 | 6.3-6.7 |

TABLE 1-continued

Exemplary A-values

| Group | −G⁰ value | |
|---|---|---|
| | kcal/mol | kJ/mol |
| —P(Ph)$_2$ | 1.8 | 7.5 |
| —C(=O)CH$_3$ | 1.02-1.52 | 4.27-6.36 |
| —C(=O)OCH$_3$ | 1.2-1.3 | 5.0-5.4 |
| —C(=O)OCH$_2$CH$_3$ | 1.1-1.2 | 4.6-5.0 |
| —CN | 0.2 | 0.84 |
| —CCH | 0.41-0.52 | 1.71-2.18 |
| —CHCH$_2$ | 1.49-1.68 | 6.23-7.0 |
| —CH$_3$ (—Me) | 1.74 | 7.28 |
| —CH$_2$CH$_3$ (—Et) | 1.79 | 7.49 |
| —CH(CH$_3$)$_2$ (—iPr) | 2.21 | 9.25 |
| —C(CH$_3$)$_3$ (—tBu) | 4.7-4.9 | 19.7-20.5 |
| —CH$_2$Ph | 1.68 | 7.03 |
| —Ph | 2.8 | 11.71 |
| —Si(CH$_3$)$_3$ | 2.5 | 10.5 |
| —C$_6$H$_{11}$ | 2.2 | 9.2 |
| —CF$_3$ | 2.4-2.5 | 10.0-10.5 |

Thus, in certain embodiments, the molecular volume of group $R^7$ is larger than the molecular volume of group $R^9$. In certain embodiments, the molecular volume of $R^7$ is at least 1.2 times greater than the molecular volume of $R^9$. In certain embodiments, the molecular volume of $R^7$ is at least 1.5 times greater than the molecular volume of $R^9$. In certain embodiments, the molecular volume of $R^7$ is at least 1.8 times greater than the molecular volume of $R^9$. In certain embodiments, the molecular volume of $R^7$ is at least 2 times greater than the molecular volume of $R^9$. In certain embodiments, the molecular volume of $R^7$ is at least 2.5 times greater than the molecular volume of $R^9$. In certain embodiments, the molecular volume of $R^7$ is at least 3 times greater than the molecular volume of $R^9$.

However, in certain embodiments, the molecular volume of group $R^9$ is larger than the molecular volume of group $R^7$. In certain embodiments, the molecular volume of $R^9$ is at least 1.2 times greater than the molecular volume of $R^7$. In certain embodiments, the molecular volume of $R^9$ is at least 1.5 times greater than the molecular volume of $R^7$. In certain embodiments, the molecular volume of $R^9$ is at least 1.8 times greater than the molecular volume of $R^7$. In certain embodiments, the molecular volume of $R^9$ is at least 2 times greater than the molecular volume of $R^7$. In certain embodiments, the molecular volume of $R^9$ is at least 2.5 times greater than the molecular volume of $R^7$. In certain embodiments, the molecular volume of $R^9$ is at least 3 times greater than the molecular volume of $R^7$.

In certain embodiments, the molecular volume of $R^7$ is greater than the molecular volume of $R^9$. In certain embodiments, the A-value of $R^7$ is at least 1.2 times greater than the A value of $R^9$. In certain embodiments, the A-value of $R^7$ is at least 1.5 times greater than the A value of $R^9$. In certain embodiments, the A-value of $R^7$ is at least 1.8 times greater than the A value of $R^9$. In certain embodiments, the A-value of $R^7$ is at least 2 times greater than the A value of $R^9$. In certain embodiments, the A-value of $R^7$ is at least 2.5 times greater than the A value of $R^9$. In certain embodiments, the A-value of $R^7$ is at least 3 times greater than the A value of $R^9$.

However, in certain embodiments, the A-value of $R^9$ is greater than the A-value of $R^7$. In certain embodiments, the A-value of $R^9$ is at least 1.2 times greater than the A value of $R^7$. In certain embodiments, the A-value of $R^9$ is at least 1.5 times greater than the A value of $R^7$. In certain embodiments, the A-value of $R^9$ is at least 1.8 times greater than the A value of $R^7$. In certain embodiments, the A-value of $R^9$ is at least 2 times greater than the A value of $R^7$. In certain embodiments, the A-value of $R^9$ is at least 2.5 times greater than the A value of $R^7$. In certain embodiments, the A-value of $R^9$ is at least 3 times greater than the A value of $R^7$.

In certain embodiments, the A-value of $R^7$ is greater than about 2.5 kcal/mol. In certain embodiments, the A-value of $R^7$ is greater than about 3 kcal/mol. In certain embodiments, the A-value of $R^7$ is greater than about 3.5 kcal/mol. In certain embodiments, the A-value of $R^7$ is greater than about 4 kcal/mol.

In certain embodiments, the A-value of $R^9$ is greater than about 2.5 kcal/mol. In certain embodiments, the A-value of $R^9$ is greater than about 3 kcal/mol. In certain embodiments, the A-value of $R^9$ is greater than about 3.5 kcal/mol. In certain embodiments, the A-value of $R^9$ is greater than about 4 kcal/mol.

In certain embodiments, the A-value of $R^9$ is between about 0 to about 2.5 kcal/mol. In certain embodiments, the A-value of $R^9$ is between about 0 to about 3 kcal/mol. In certain embodiments, the A-value of $R^9$ is between about 0 to about 3.5 kcal/mol. In certain embodiments, the A-value of $R^9$ is between about 0 to about 4 kcal/mol.

In certain embodiments, the A-value of $R^7$ is between about 0 to about 2.5 kcal/mol. In certain embodiments, the A-value of $R^7$ is between about 0 to about 3 kcal/mol. In certain embodiments, the A-value of $R^7$ is between about 0 to about 3.5 kcal/mol. In certain embodiments, the A-value of $R^7$ is between about 0 to about 4 kcal/mol.

In certain embodiments, the Southern Hemisphere of the metal complex is of the formula (ii-e):

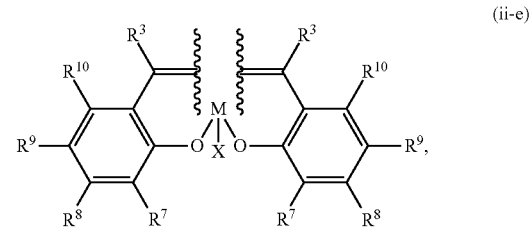

(ii-e)

wherein M, X, $R^1$, $R^2$, $R^3$, $R^7$, $R^8$, $R^9$, and $R^{10}$ are, as defined above and herein.

In certain embodiments of formula (ii-e), wherein $R^3$, $R^8$ and $R^{10}$ are hydrogen, the Southern Hemisphere of the metal complex is of the formula (ii-f):

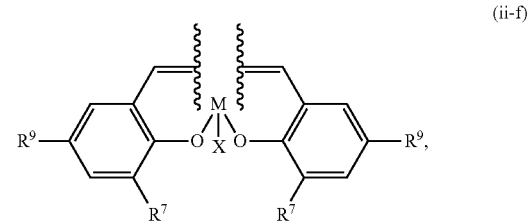

(ii-f)

wherein M, X, $R^7$ and $R^9$ are as defined above and herein.

In certain embodiments, M is a metal selected from cobalt and chromium. In certain embodiments, M is cobalt. In certain embodiments, M is cobalt (III).

In certain embodiments, $R^7$ is not —C(CH$_3$)$_2$Ph. In certain embodiments, $R^7$ is not —[C(CH$_3$)$_2$CH$_2$CH$_2$N(Bu)$_3$]$^+$. In certain embodiments, $R^7$ is not —CH(CH$_2$CH$_3$)C$_6$H$_5$. In certain embodiments, $R^7$ is not —$C(CH_3)_2CH_2C(CH_3)_3$. In certain embodiments, $R^7$ is not —$CH(C_6H_5)CHCH_2$. In certain embodiments, $R^7$ is not —$C(CH_3)_2CH_2CH_3$. In certain embodiments, $R^7$ is not 1-methyl-cyclohexyl. In certain embodiments, $R^7$ is not cyclohexyl.

In certain embodiments, $R^9$ is not —$C(CH_3)_2C_6H_5$. In certain embodiments, $R^9$ is not —$[C(CH_3)_2CH_2CH_2N(Bu)_3]^+$. In certain embodiments, $R^9$ is not —$C(CH_3)_2CH_2C(CH_3)_3$. In certain embodiments, $R^9$ is not —$C(CH_3)_3$. In certain embodiments, $R^9$ is not —$C(CH_3)_2CH_2CH_3$. In certain embodiments, $R^9$ is not —$CH_3$. In certain embodiments, $R^9$ is not hydrogen.

In some embodiments, when $R^7$ is —$C(CH_3)_2Ph$, $R^9$ is other than —$C(CH_3)_2Ph$. In some embodiments, when $R^7$ is —$[C(CH_3)_2CH_2CH_2N(Bu)_3]^+$, $R^9$ is other than —$[C(CH_3)_2CH_2CH_2N(Bu)_3]^+$. In some embodiments, when $R^7$ is —$CH(CH_2CH_3)C_6H_5$, $R^9$ is other than hydrogen. In some embodiments, when $R^7$ is —$C(CH_3)_2CH_2C(CH_3)_3$, $R^9$ is other than —$C(CH_3)_2CH_2C(CH_3)_3$. In some embodiments, when $R^7$ is —$CH(C_6H_5)CHCH_2$, $R^9$ is other than —$C(CH_3)_3$. In some embodiments, when $R^7$ is —$C(CH_3)_2CH_2CH_3$, $R^9$ is other than —$C(CH_3)_3$. In some embodiments, when $R^7$ is —$C(CH_3)_2CH_2CH_3$, $R^9$ is other than —$C(CH_3)_2CH_2CH_3$. In some embodiments, when $R^7$ is 1-methyl-cyclohexyl, $R^9$ is other than —$C(CH_3)_3$. In some embodiments, when $R^7$ is 1-methyl-cyclohexyl, $R^9$ is other than —$C(CH_3)_2CH_2CH_3$. In some embodiments, when $R^7$ is cyclohexyl, $R^9$ is other than —$CH_3$.

In certain embodiments, the Southern Hemisphere is not selected from:

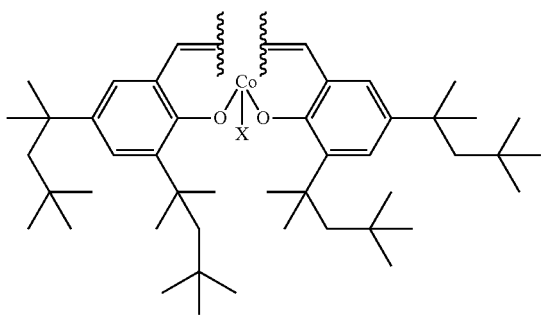

,

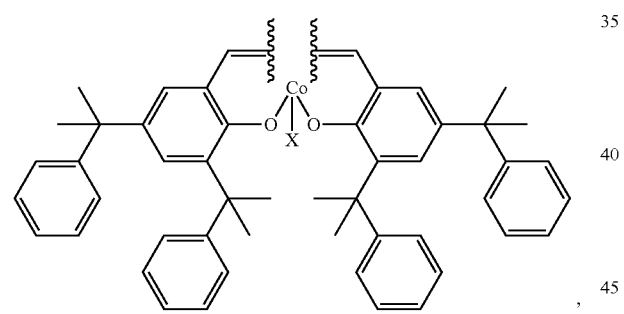

,

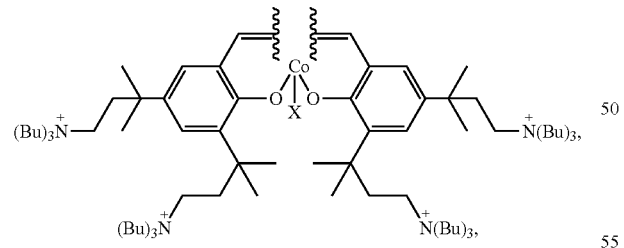

,

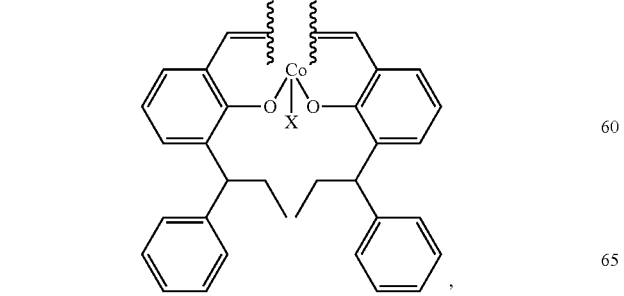

,

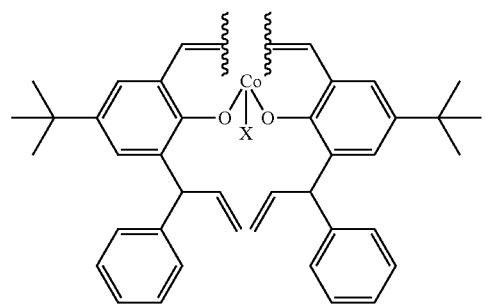

,

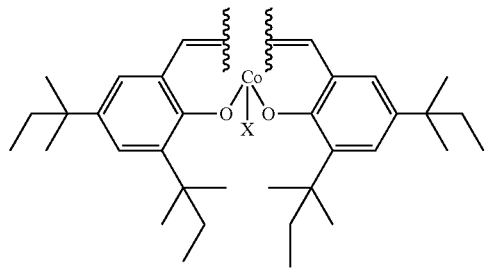

,

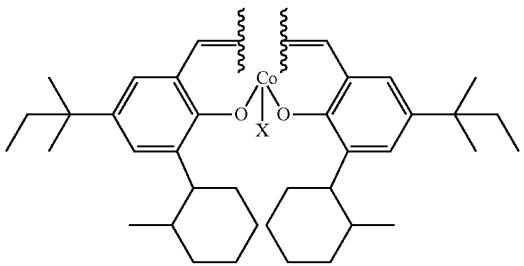

,

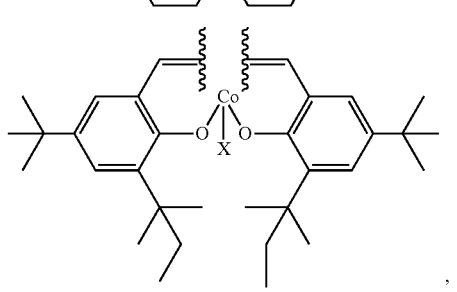

,

-continued

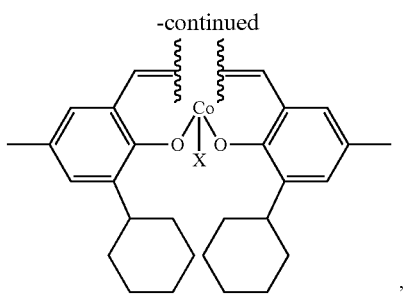

wherein X is as defined above and herein.

Any of the above formulae (i-a) to (i-q) may be combined with any of the above formulae (ii-a) to (ii-f) to provide novel metal complexes.

For example, in certain embodiments, the present disclosure provides a metal complex of the formula (I-a):

(I-a)

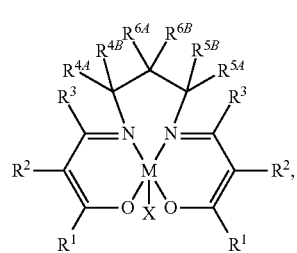

wherein M, X, $R^1$, $R^2$, $R^3$, $R^{4A}$, $R^{4B}$, $R^{5A}$, $R^{5B}$, $R^{6A}$, and $R^{6B}$ are as defined above and herein.

In certain embodiments, the present disclosure provides a metal complex of the formula (I-b):

(I-b)

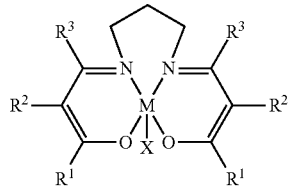

wherein M, X, $R^1$, $R^2$ and $R^3$ are as defined above and herein.

In certain embodiments, the present disclosure provides a metal complex of the formula (I-c):

(I-c)

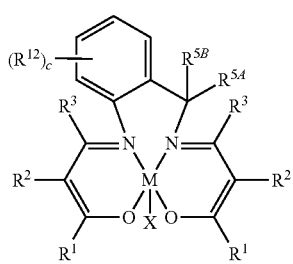

wherein M, X, $R^1$, $R^2$, $R^3$, $R^{5A}$, $R^{5B}$, $R^{12}$ and c are as defined above and herein.

In certain embodiments, the present disclosure provides a metal complex of the formula (I-d):

(I-d)

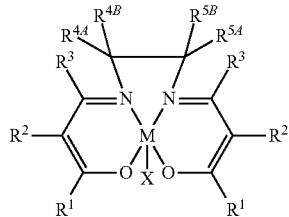

wherein M, X, $R^1$, $R^2$, $R^3$, $R^{4A}$, $R^{4B}$, $R^{5A}$, and $R^{5B}$ are as defined above and herein.

In certain embodiments, the present disclosure provides a metal complex of the formula (I-e):

(I-e)

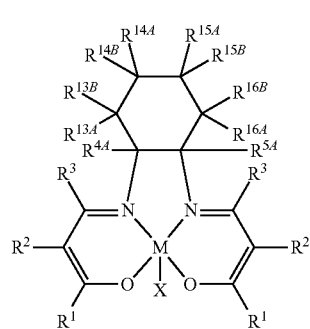

wherein M, X, $R^1$, $R^2$, $R^3$, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are as defined above and herein.

In certain embodiments, the present disclosure provides a metal complex of any one of the formulae (I-f) to (I-i):

(I-f)

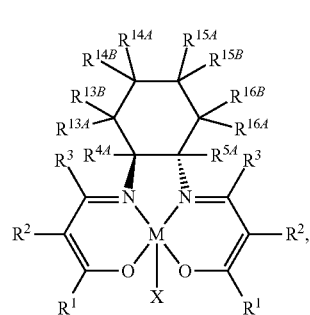

(I-g)

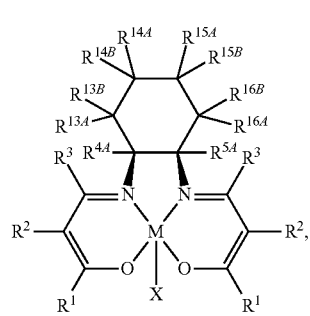

-continued

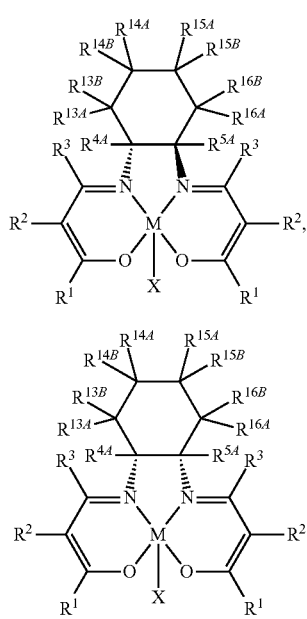

(I-h)

(I-i)

or any mixture thereof;
wherein M, X, $R^1$, $R^2$, $R^3$, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are as defined above and herein.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer.

Thus, in certain embodiments, the present disclosure provides an optically enriched metal complex of any one of the formulae (I-f) to (I-i). In certain embodiments, the present disclosure provides an optically enriched metal complex of formula (I-f). In certain embodiments, the present disclosure provides an optically enriched metal complex of formula (I-g). In certain embodiments, the present disclosure provides an optically enriched metal complex of formula (I-h). In certain embodiments, the present disclosure provides an optically enriched metal complex of formula (I-i).

In certain embodiments, the present disclosure provides a metal complex of the formula (I-j):

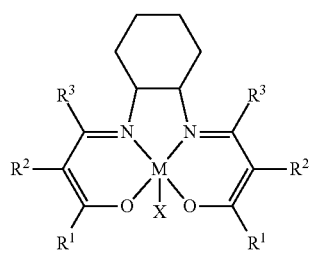

(I-j)

wherein M, X, $R^1$, $R^2$ and $R^3$ are as defined above and herein.

In certain embodiments, the present disclosure provides a metal complex of any one of the formulae (I-k) to (I-n):

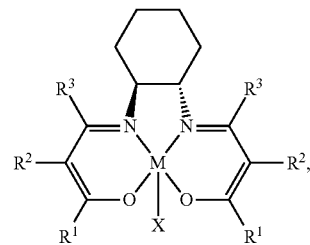

(I-k)

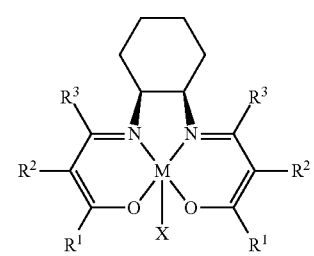

(I-l)

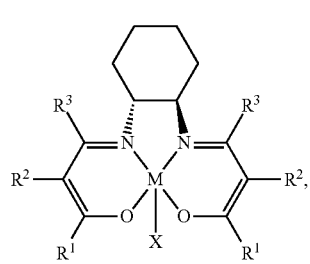

(I-m)

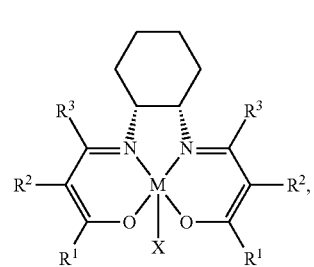

(I-n)

or any mixture thereof;
wherein M, X, $R^1$, $R^2$ and $R^3$ are as defined above and herein.

In certain embodiments, the present disclosure provides an optically enriched metal complex of any one of the formulae (I-k) to (I-n). In certain embodiments, the present disclosure provides an optically enriched metal complex of formula (I-k). In certain embodiments, the present disclosure provides an optically enriched metal complex of formula (I-l). In certain embodiments, the present disclosure provides an optically enriched metal complex of formula (I-m). In certain embodiments, the present disclosure provides an optically enriched metal complex of formula (I-n).

In certain embodiments, the present disclosure provides a metal complex of the formula (I-o):

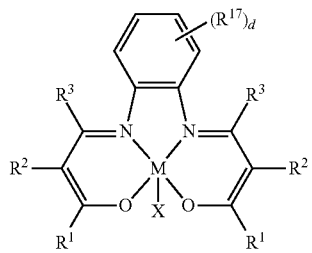

(I-o)

wherein d, M, X, $R^1$, $R^2$, $R^3$ and $R^{17}$ are as defined above and herein.

In certain embodiments, the present disclosure provides a metal complex of the formula (I-p):

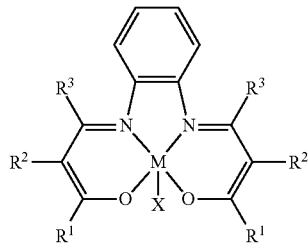

(I-p)

wherein d, M, X, $R^1$, $R^2$ and $R^3$ are as defined above and herein.

In certain embodiments, the present disclosure provides a metal complex of the formula (I-q):

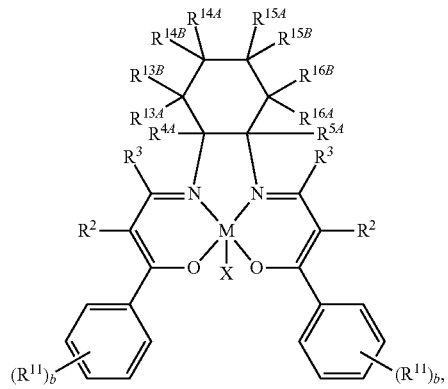

(I-q)

wherein b, M, X, $R^1$, $R^2$, $R^3$, $R^{11}$, $R^{4A}$, $R^{5A}$, $R^{13A}$, $R^{13B}$, $R^{14A}$, $R^{14B}$, $R^{15A}$, $R^{15B}$, $R^{16A}$, $R^{16B}$ are as defined above and herein.

In certain embodiments, the present disclosure provides a metal complex of the formula (I-r):

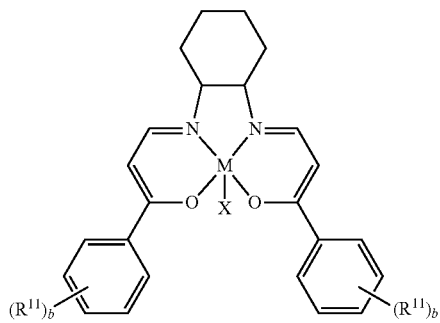

(I-r)

wherein b, $R^{11}$, M and X are as defined above and herein.

In certain embodiments, the present disclosure provides a metal complex of the formula (I-s):

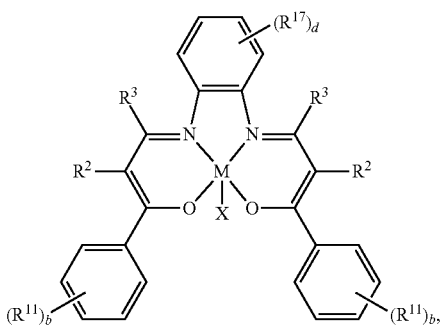

(I-s)

wherein b, d, M, X, $R^1$, $R^2$, $R^3$, $R^{11}$ and $R^{17}$ are as defined above and herein.

In certain embodiments, the present disclosure provides a metal complex of the formula (I-t):

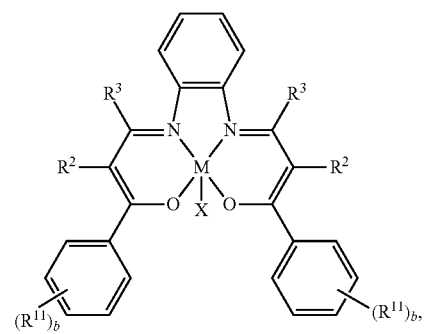

(I-t)

wherein b, M, X, $R^1$, $R^2$, $R^3$ and $R^{11}$ are as defined above and herein.

In certain embodiments, the present disclosure provides a metal complex of the formula (I-u):

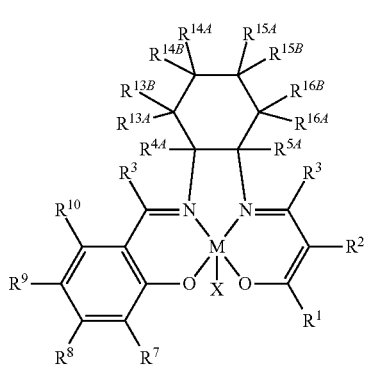

(I-u)

wherein M, X, $R^1$, $R^2$, $R^3$, $R^{4A}$, $R^{5A}$, $R^7$, $R^8$, $R^9$, $R^{10}$, $R^{13A}$, $R^{13B}$, $R^{14A}$, $R^{14B}$, $R^{15A}$, $R^{15B}$, $R^{16A}$, $R^{16B}$ are as defined above and herein.

In certain embodiments, the present disclosure provides a metal complex of the formula (I-v):

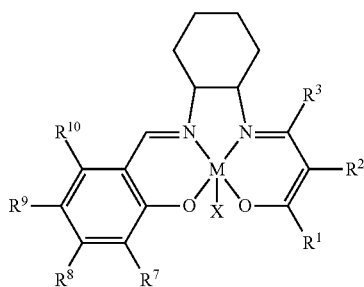

(I-v)

wherein M, X, $R^1$, $R^2$, $R^3$, $R^7$, $R^8$, $R^9$ and $R^{10}$ are as defined above and herein.

In certain embodiments, the present disclosure provides a metal complex of the formula (I-w):

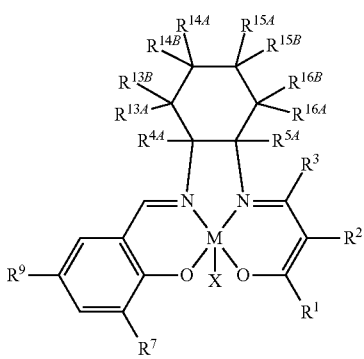

(I-w)

wherein M, X, $R^1$, $R^2$, $R^3$, $R^{4A}$, $R^{5A}$, $R^7$, $R^9$, $R^{13A}$, $R^{13B}$, $R^{14A}$, $R^{14B}$, $R^{15A}$, $R^{15B}$, $R^{16A}$, $R^{16B}$ are as defined above and herein.

In certain embodiments, the present disclosure provides a metal complex of the formula (I-x):

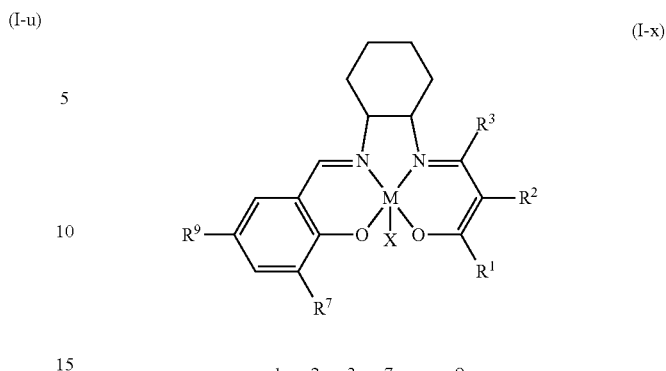

(I-x)

wherein M, X, $R^1$, $R^2$, $R^3$, $R^7$ and $R^9$ are as defined above and herein.

In certain embodiments, the present disclosure provides a metal complex of the formula (I-y):

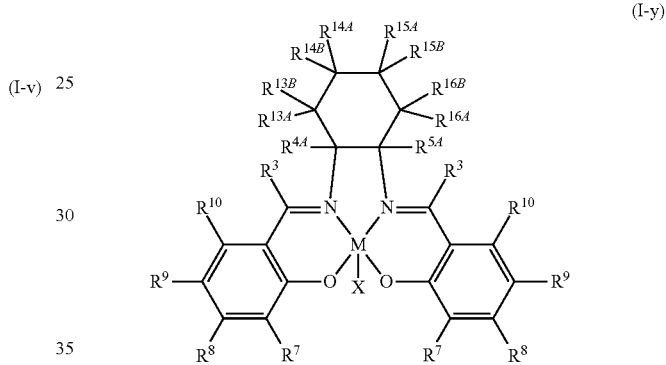

(I-y)

wherein M, X, $R^{4A}$, $R^{5A}$, $R^7$, $R^8$, $R^9$, $R^{13A}$, $R^{13B}$, $R^{14A}$, $R^{14B}$, $R^{15A}$, $R^{15B}$, $R^{16A}$, $R^{16B}$ are as defined above and herein.

In certain embodiments, the present disclosure provides a metal complex of the formula (I-z):

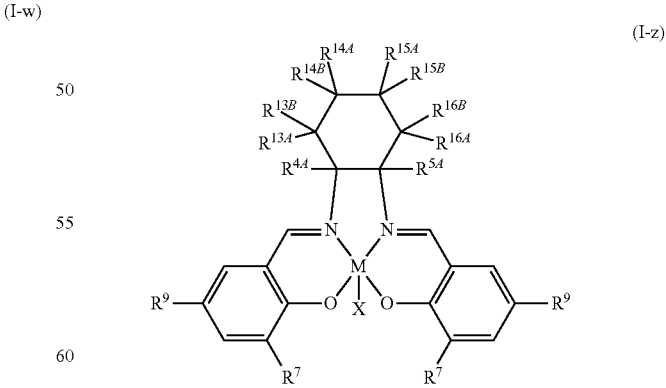

(I-z)

wherein M, X, $R^{4A}$, $R^{5A}$, $R^7$, $R^9$, $R^{13A}$, $R^{13B}$, $R^{14A}$, $R^{14B}$, $R^{15A}$, $R^{15B}$, $R^{16A}$, $R^{16B}$ are as defined above and herein.

In certain embodiments, the present disclosure provides a metal complex of the formula (I-aa):

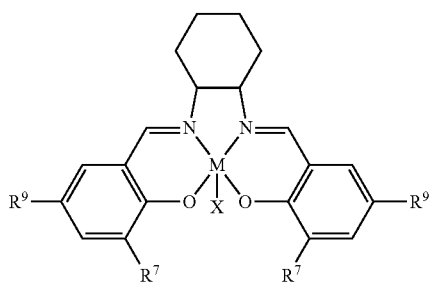
(I-aa)

wherein M, X, $R^7$ and $R^9$ are as defined above and herein.

In certain embodiments, the present disclosure provides a metal complex of the formulae (I-bb) to (I-ee):

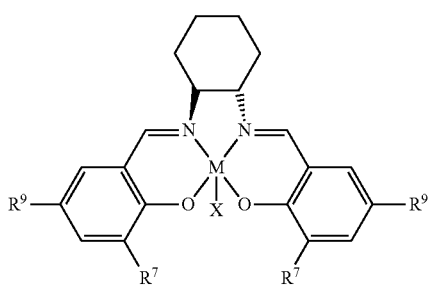
(I-bb)

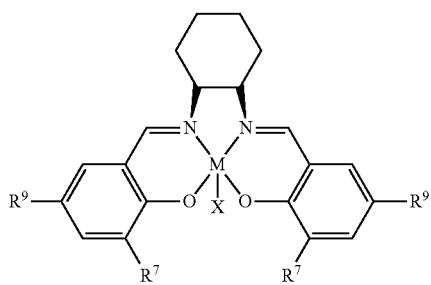
(I-cc)

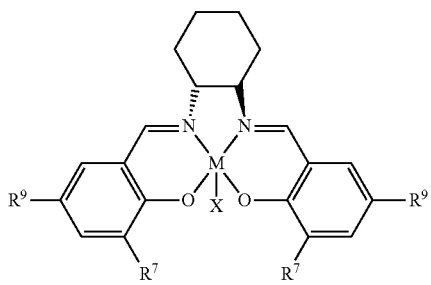
(I-dd)

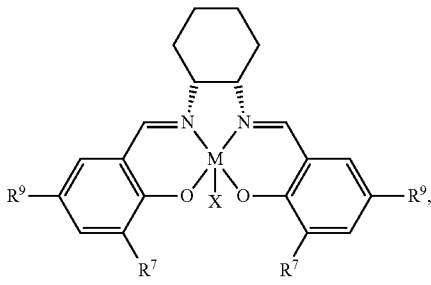
(I-ee)

or any mixture thereof.

In certain embodiments, the present disclosure provides an optically enriched metal complex of any one of the formulae (I-bb) to (I-ee). In certain embodiments, the present disclosure provides an optically enriched metal complex of formula (I-bb). In certain embodiments, the present disclosure provides an optically enriched metal complex of formula (I-cc). In certain embodiments, the present disclosure provides an optically enriched metal complex of formula (I-dd). In certain embodiments, the present disclosure provides an optically enriched metal complex of formula (I-ee).

In certain embodiments, the present disclosure provides a metal complex of the formula (I-ff):

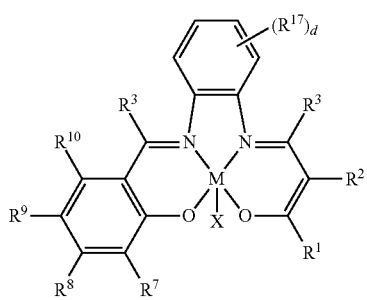
(I-ff)

wherein d, M, X, $R^1$, $R^2$, $R^3$, $R^{4A}$, $R^{5A}$, $R^7$, $R^8$, $R^9$, $R^{10}$ and $R^{17}$ are as defined above and herein.

In certain embodiments, the present disclosure provides a metal complex of the formula (I-gg):

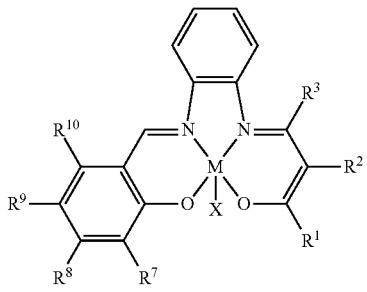
(I-gg)

wherein M, X, $R^1$, $R^2$, $R^3$, $R^7$, $R^8$, $R^9$ and $R^{10}$ are as defined above and herein.

In certain embodiments, the present disclosure provides a metal complex of the formula (I-hh):

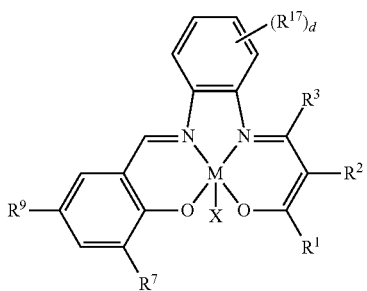
(I-hh)

wherein d, M, X, $R^1$, $R^2$, $R^3$, $R^7$, $R^9$ and $R^{17}$ are as defined above and herein.

In certain embodiments, the present disclosure provides a metal complex of the formula (I-ii):

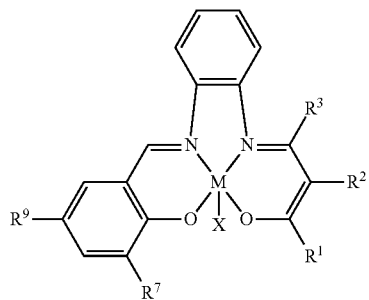
(I-ii)

wherein M, X, $R^1$, $R^2$, $R^3$, $R^7$ and $R^9$ are as defined above and herein.

In certain embodiments, the present disclosure provides a metal complex of the formula (I-jj):

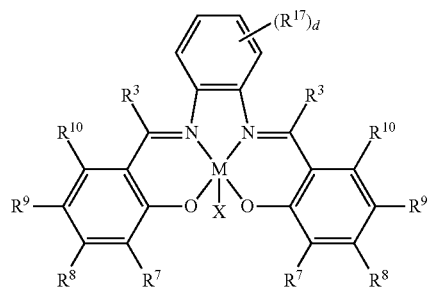
(I-jj)

wherein d, M, X, $R^{4A}$, $R^{5A}$, $R^7$, $R^8$, $R^9$, $R^{10}$ and $R^{17}$ are as defined above and herein.

In certain embodiments, the present disclosure provides a metal complex of the formula (I-kk):

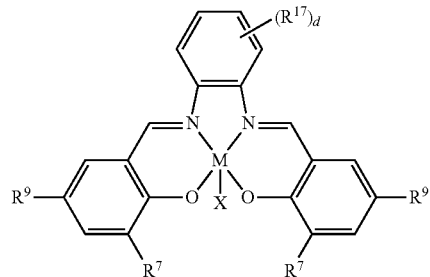
(I-kk)

wherein d, M, X, $R^7$, $R^9$ and $R^{17}$ are as defined above and herein.

In certain embodiments, the present disclosure provides a metal complex of the formula (I-ll):

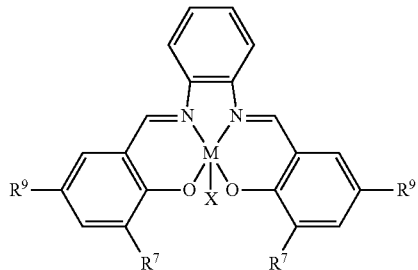
(I-ll)

wherein M, X, $R^7$ and $R^9$ are as defined above and herein.

In certain embodiments, the present disclosure provides a metal complex of the formula (I-mm):

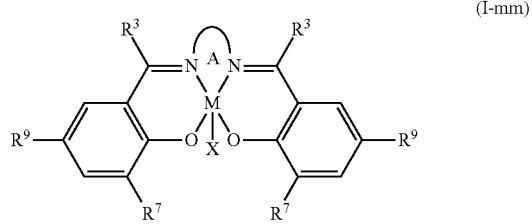
(I-mm)

wherein M, X, Ring A, $R^3$, $R^7$ and $R^9$ are as defined above and herein.

In certain embodiments, the present disclosure provides a metal complex of the formula (I-nn):

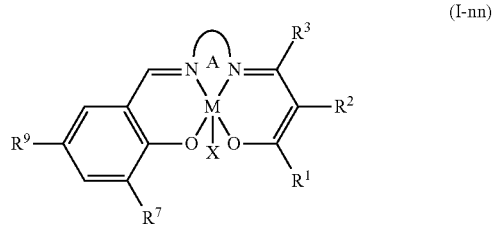
(I-nn)

wherein M, X, Ring A, $R^1$, $R^2$, $R^3$, $R^7$ and $R^9$ are as defined above and herein.

In certain embodiments, the present disclosure provides a metal complex of the formula (I-oo):

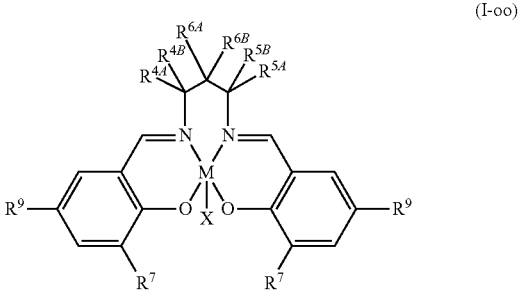
(I-oo)

wherein M, X, $R^7$, $R^9$, $R^{4A}$, $R^{4B}$, $R^{5A}$, $R^{5B}$, and $R^{6A}$, $R^{6B}$ are as defined above and herein.

III. Exemplary Metal Complexes
In certain embodiments, the metal complex is selected from any one of the following, wherein X is absent or is a nucleophilic ligand:
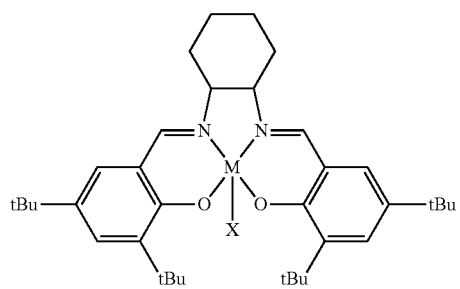
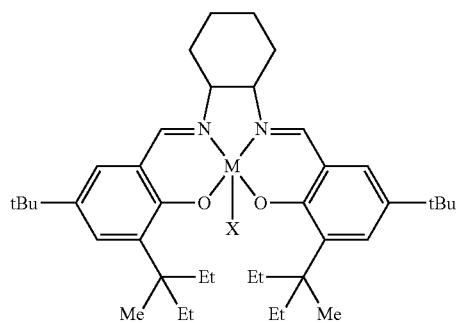
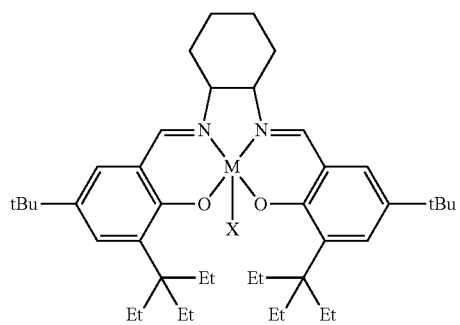
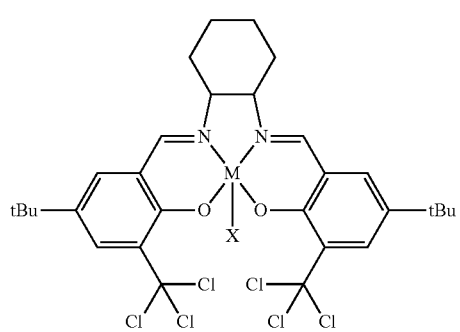
-continued
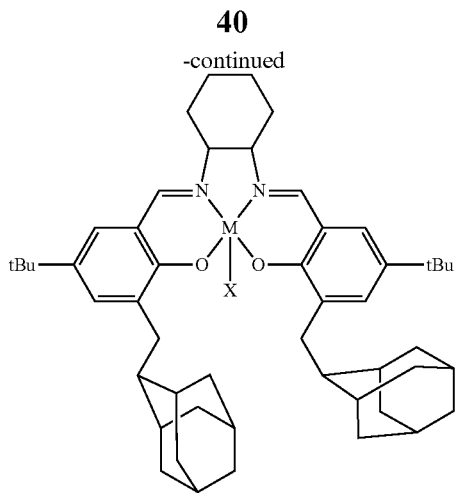
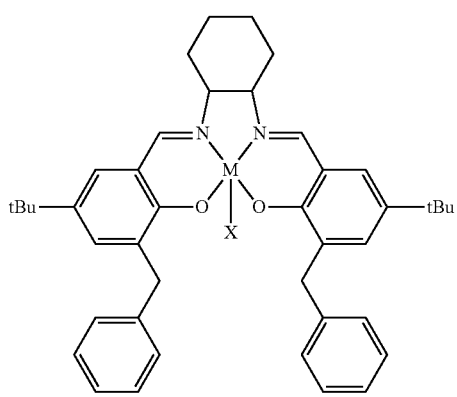
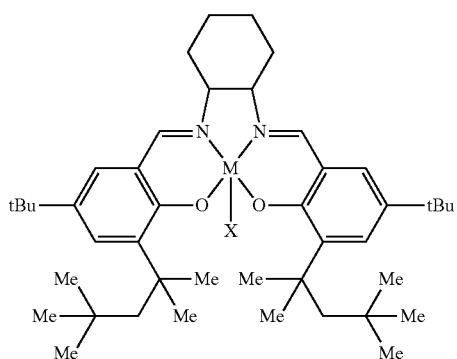
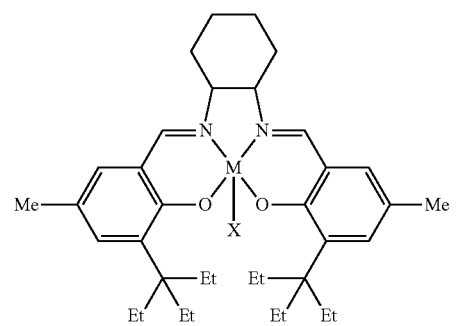

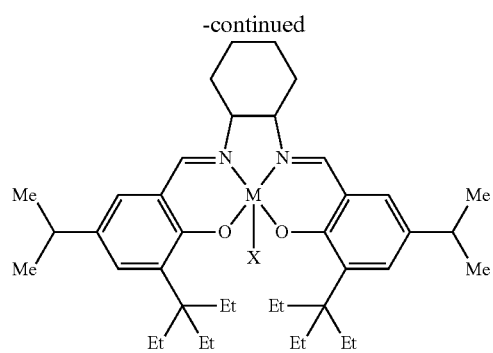
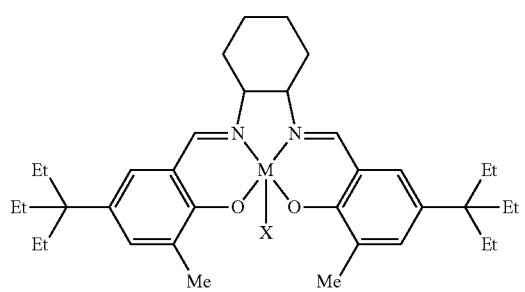
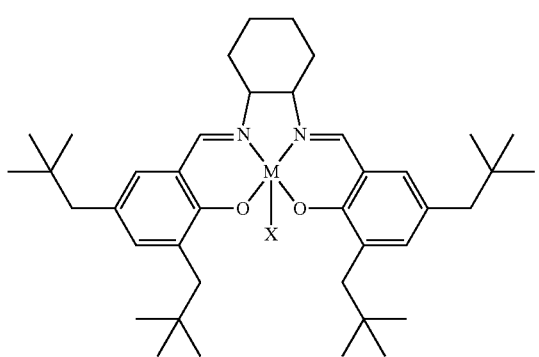
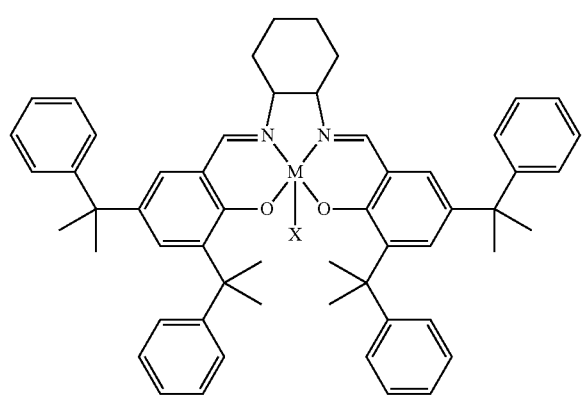
In certain embodiments, the metal complex is selected from any one of the following, wherein X is absent or is a nucleophilic ligand:
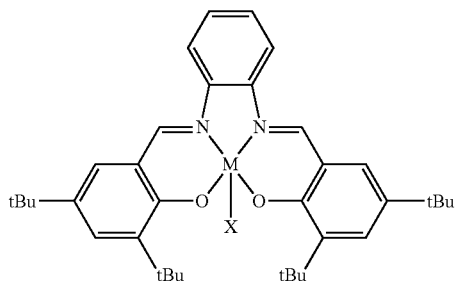
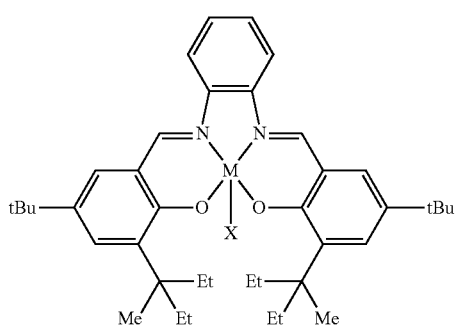
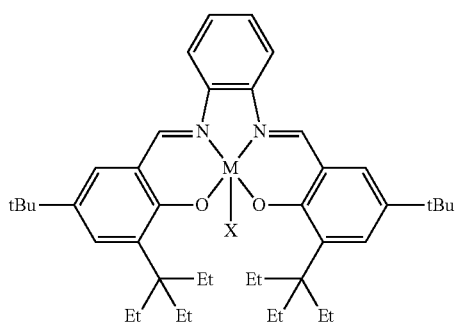
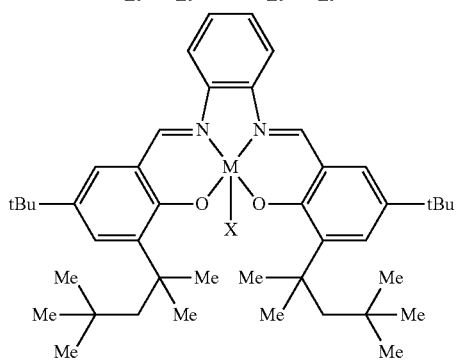
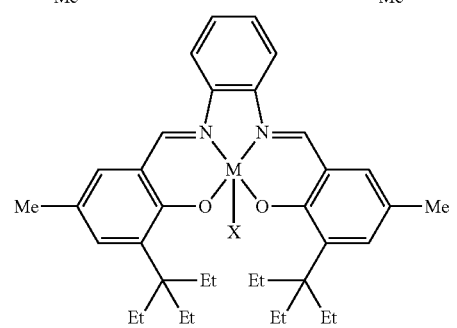

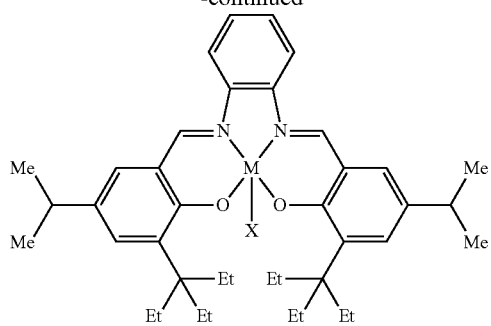
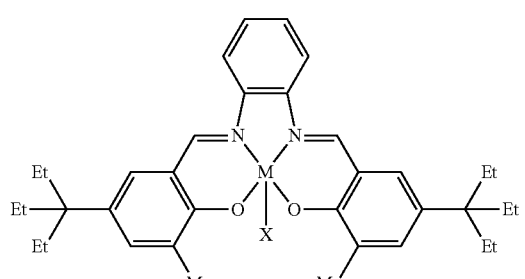
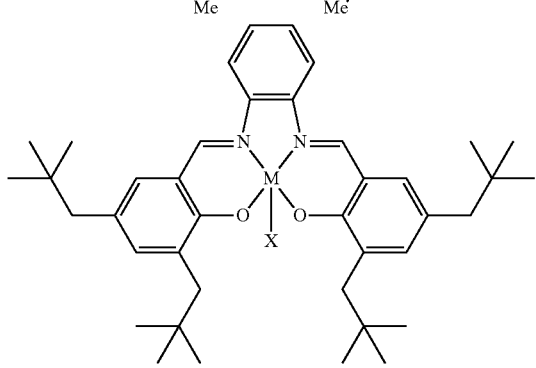
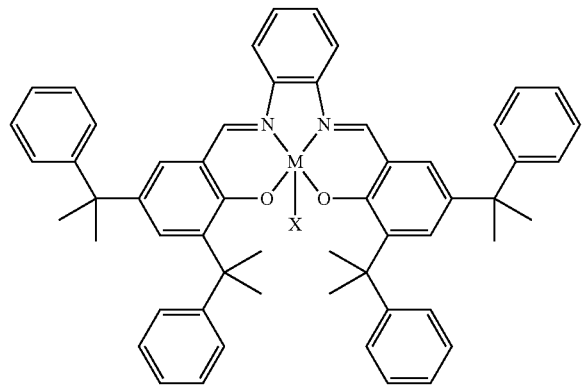
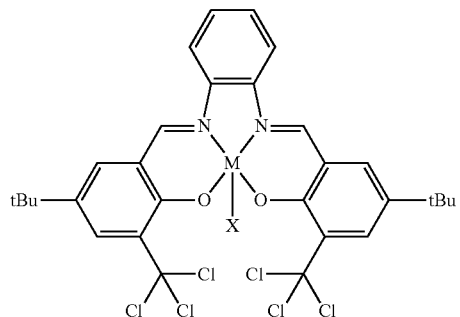
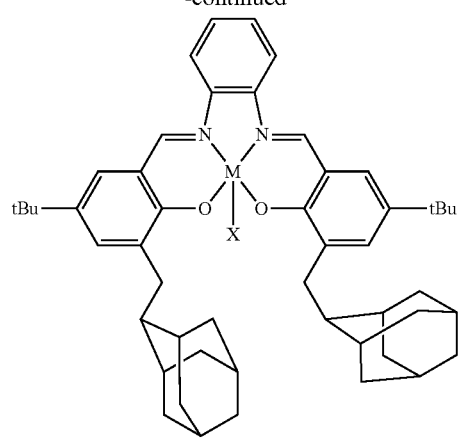
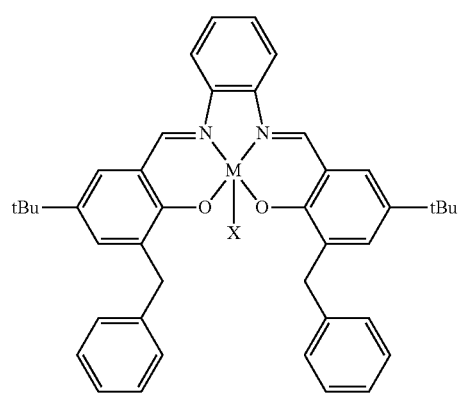
In certain embodiments, the metal complex has the following structure, wherein X is absent or is a nucleophilic ligand:
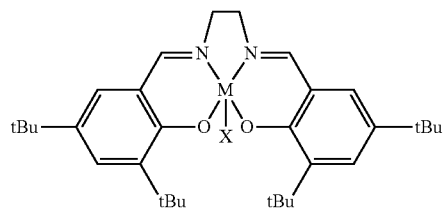
In certain embodiments, the metal complex has the following structure, wherein X is absent or is a nucleophilic ligand:
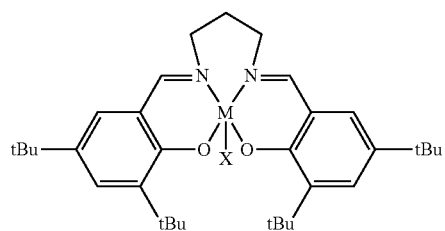
In certain embodiments, the metal complex has the following structure, wherein X is absent or is a nucleophilic ligand:

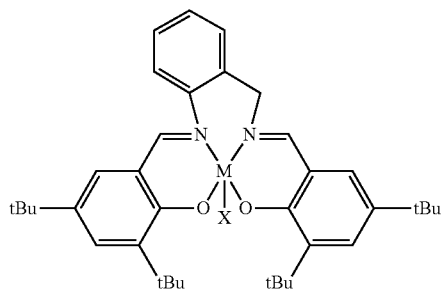

In certain embodiments, the metal complex has the following structure, wherein X is absent or is a nucleophilic ligand:

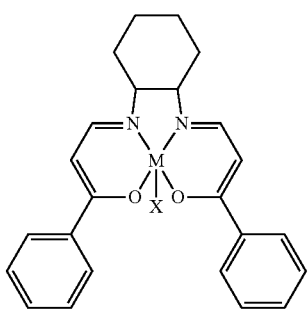

In certain embodiments, the metal complex has the following structure, wherein X is absent or is a nucleophilic ligand:

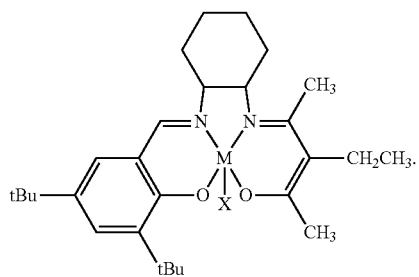

In certain embodiments, X is absent.

In certain embodiments, X is —O(C=O)$C_6F_5$ (i.e., —OBzF$_5$). In certain embodiments, X is —OC(=O)$CH_3$. In certain embodiments, X is —OC(=O)$CF_3$. In certain embodiments, X is —NC. In certain embodiments, X is —Cl. In certain embodiments, X is —Br. In certain embodiments, X is $N_3$.

In certain embodiments, the metal complex is a cobalt (Co) complex selected from any of the following structures:

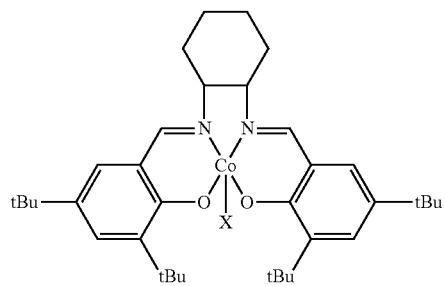

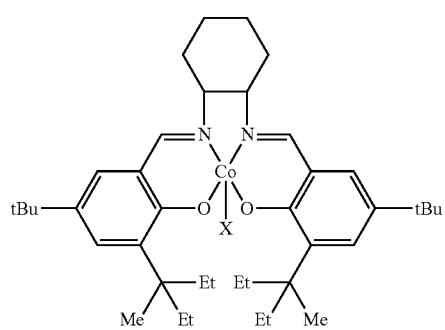

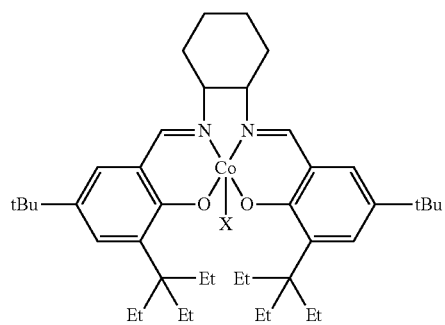

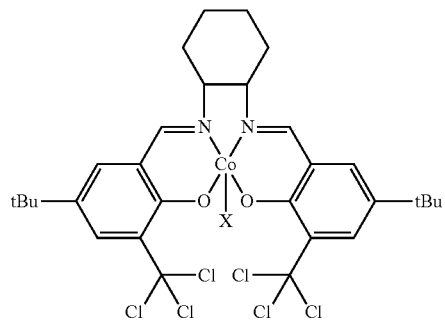

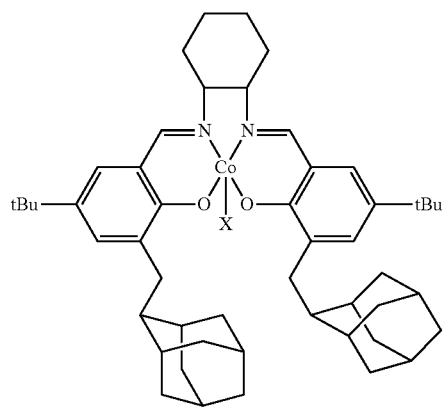

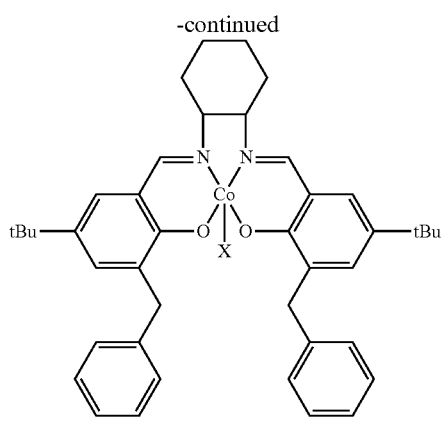
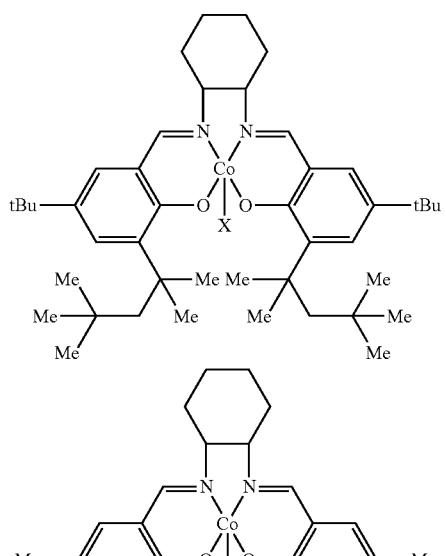
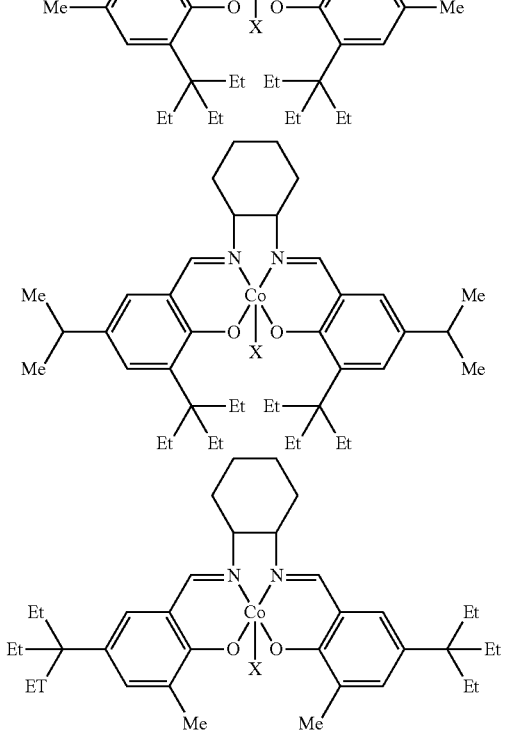
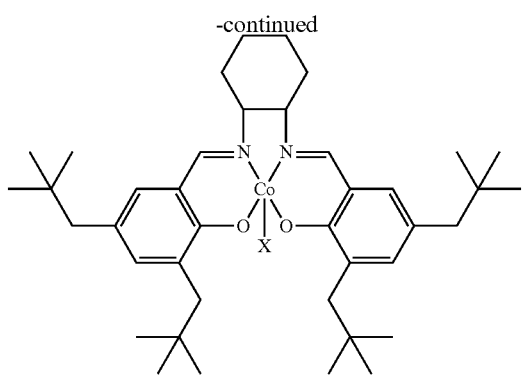
In certain embodiments, the metal complex is a cobalt (Co) complex selected from any of the following structures:
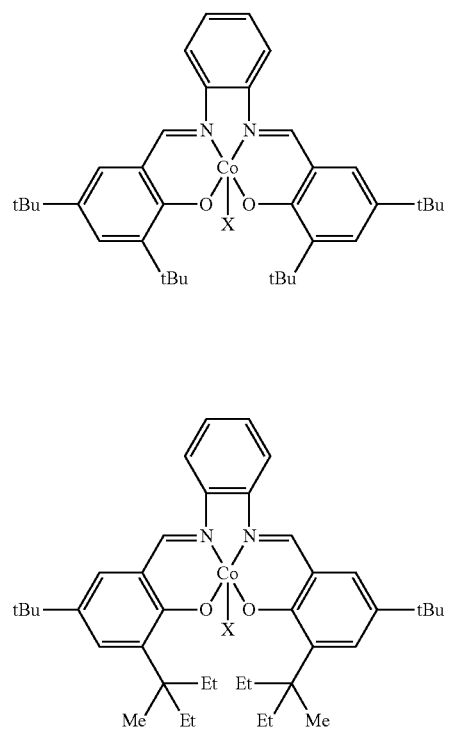

49
-continued
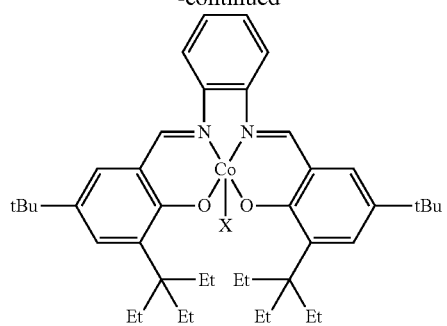
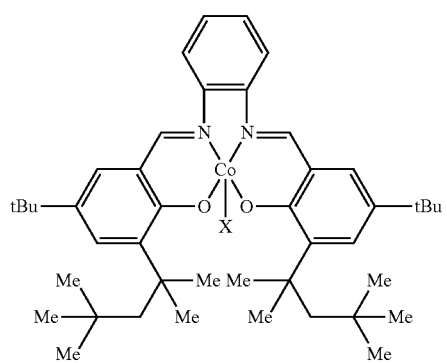
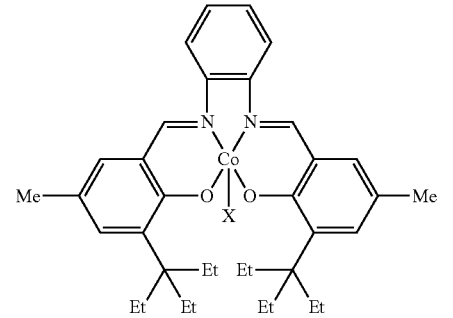
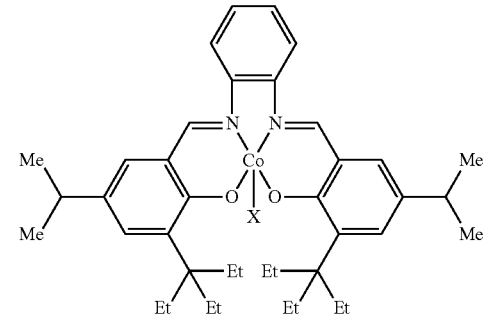
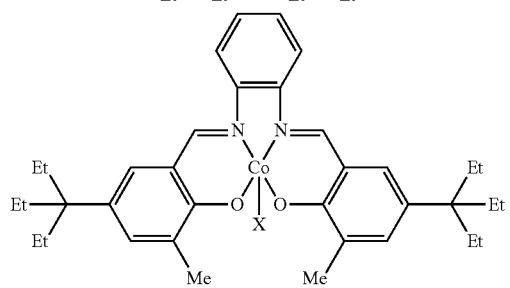
50
-continued
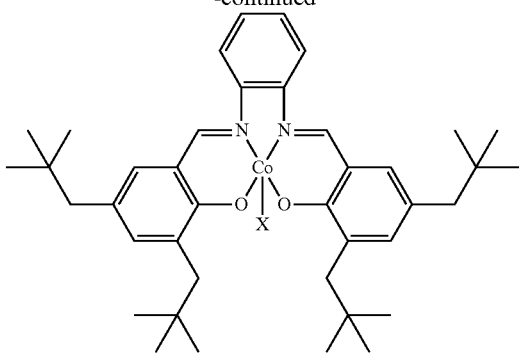
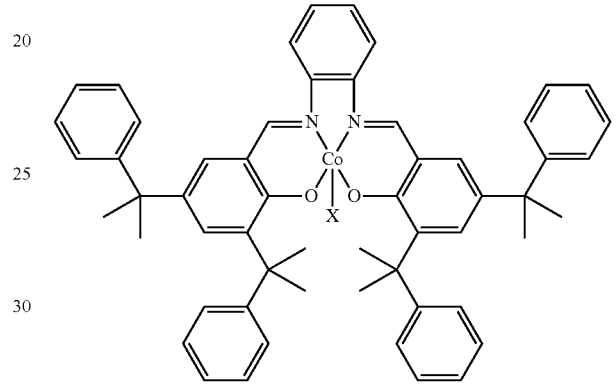
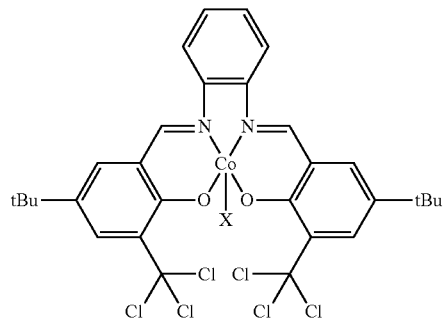
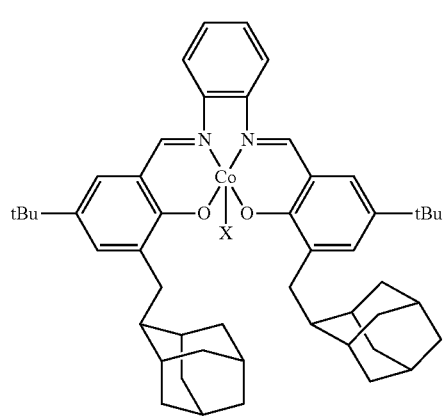

-continued

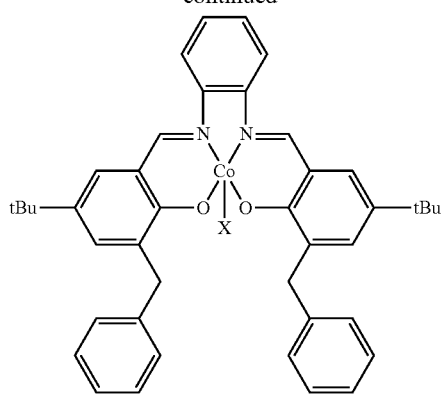

In certain embodiments, the metal complex is a cobalt (Co) complex having the following structure:

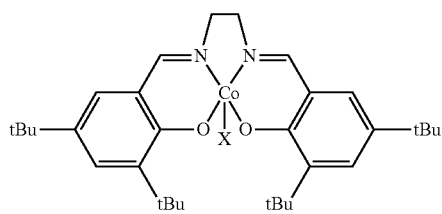

In certain embodiments, the metal complex is a cobalt (Co) complex having the following structure:

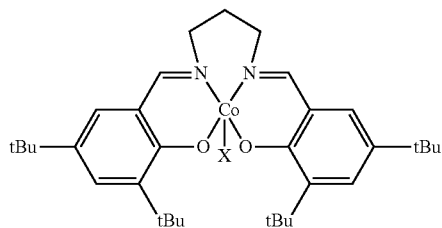

In certain embodiments, the metal complex is a cobalt (Co) complex having the following structure:

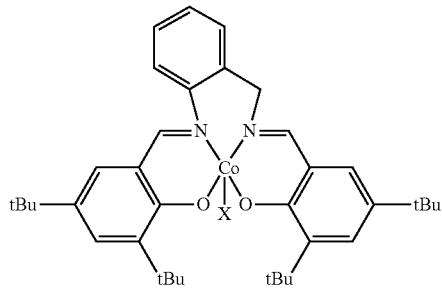

In certain embodiments, the metal complex is a cobalt (Co) complex having the following structure:

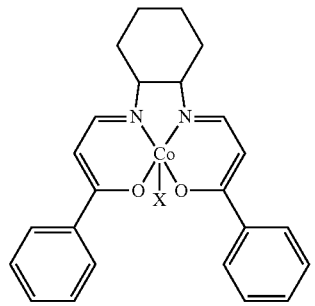

In certain embodiments, the metal complex is a cobalt (Co) complex having the following structure:

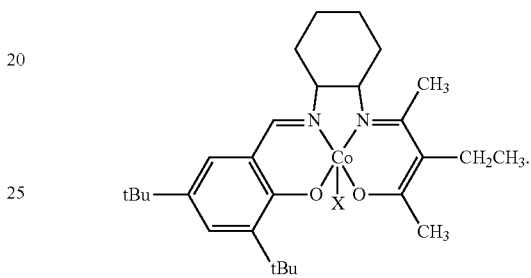

IV. Methods of Making Poly(Ethylene Carbonate) Polymers

The present disclosure also provides methods of making various poly(ethylene carbonate) polymers. As used herein, poly(ethylene carbonate) polymers are provided via polymerization of ethylene oxide (EO) and carbon dioxide ($CO_2$) in the presence of a metal complex, and encompass encompasses poly(ethylene carbonate) (PEC), as well as polymers which comprise poly(ethylene carbonate), such as, for example, polyethylene oxide-co-polyethylene carbonate.

For example, in one aspect, the present disclosure provide a method of synthesizing a poly(ethylene carbonate) polymer, wherein the polymer is made up of Y, and optionally Z, and wherein the percentage of Y is greater than the percentage of Z,

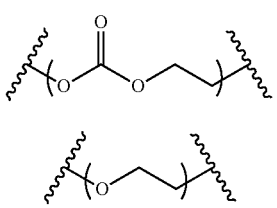

the method comprising reacting ethylene oxide and carbon dioxide in the presence of a metal complex.

In certain embodiments, the polymer has greater than about 85 percent of Y. In certain embodiments, the polymer has greater than about 90% of Y. In certain embodiments, the polymer has greater than about 95% of Y. In certain embodiments, the polymer has greater than about 99% of Y. In certain embodiments, the polymer is substantially all Y and is substantially free of Z.

In certain embodiments, the polymer is an alternating polymer of ethylene oxide and carbon dioxide (e.g., with regular alternating units of ethylene oxide and carbon dioxide).

For example, wherein the polymer is substantially all Y and is substantially free of Z, the polymer an alternating polymer of the formula:

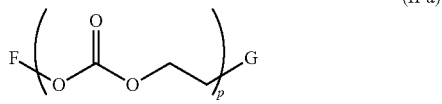

(II-a)

wherein P is an integer of between about 10 and about 15,000, inclusive, and each F and G are, independently, a suitable terminating group.

In certain embodiments, F is hydrogen. In certain embodiments F is a hydroxyl-protecting group. In certain embodiments F is an acyl group. In certain embodiments F is a silyl group. In certain embodiments, G is X, where X is as described above. In certain embodiments, G is a hydroxyl group.

In certain embodiments, P is an integer of between about 10,000 to about 15,000, inclusive. In certain embodiments, P is an integer of between about 12,000 to about 15,000, inclusive.

In certain embodiments, the metal complex is a zinc, cobalt, chromium, aluminum, titanium, ruthenium or manganese complex. In certain embodiments, the metal complex is an aluminum complex. In certain embodiments, the metal complex is a chromium complex. In certain embodiments, the complex metal is zinc complex. In certain embodiments, the metal complex is a titanium complex. In certain embodiments, the metal complex is a ruthenium complex. In certain embodiments, the metal complex is a manganese complex. In certain embodiments, the metal complex is cobalt complex. In certain embodiments, wherein the metal complex is a cobalt complex, the cobalt metal has a valency of +3 (i.e., Co(III)).

In certain embodiments, the metal complex is any of the above described metal complexes of the formula (I), or subsets thereof.

In another aspect, the present disclosure provides a method of synthesizing a poly(ethylene carbonate) polymer, the method comprising the step of reacting ethylene oxide with carbon dioxide in the presence of a cobalt complex of any of the above described metal complexes of the formula (I), or a subset thereof, wherein M is cobalt.

Reaction Conditions

In certain embodiments, any of the above methods further comprise a co-catalyst.

In certain embodiments, the co-catalyst is a Lewis base. Exemplary Lewis bases include, but are not limited to: N-methylimidazole (N-MeIm), dimethylaminopyridine (DMAP), 1,4-diazabicyclo[2.2.2]octane (DABCO), triethyl amine, and diisopropyl ethyl amine.

In certain embodiments, the co-catalyst is a salt. In certain embodiments, the co-catalyst is an ammonium salt, a phosphonium salt or an arsonium salt. In certain embodiments, the co-catalyst is an ammonium salt. Exemplary ammonium salts include, but are not limited to: $(n-Bu)_4NCl$, $(n-Bu)_4NBr$, $(n-Bu)_4NN_3$, [PPN]Cl, [PPN]Br, and [PPN]N$_3$, Ph$_3$PCPh$_3$]Cl [PPN]O(C=O)R$^e$ (PPN=Bis(triphenylphosphoranylidene) ammonium)). In certain embodiments, the co-catalyst is a phosphonium salt. In certain embodiments, the co-catalyst is an arsonium salt.

In certain embodiments, the co-catalyst is the ammonium salt bis(triphenylphosphoranylidene)ammonium chloride ([PPN]Cl).

In certain embodiments, the anion of the salt co-catalyst has the same structure as the ligand X of the above described metal complexes of the formula (I), or subsets thereof, wherein X is a nucleophilic ligand. For example, in certain embodiments, the co-catalyst is ([PPN]X) or $(n-Bu)_4NX$.

In certain embodiments, any of the above methods comprise a ratio of about 500:1 to about 500,000:1 of ethylene oxide to metal complex. In certain embodiments, any of the above methods comprise a ratio of about 500:1 to about 100,000:1 of ethylene oxide to metal complex. In certain embodiments, any of the above methods comprise a ratio of about 500:1 to about 50,000:1 of ethylene oxide to metal complex. In certain embodiments, any of the above methods comprise a ratio of about 500:1 to about 5,000:1 of ethylene oxide to metal complex. In certain embodiments, any of the above methods comprise a ratio of about 500:1 to about 1,000:1 of ethylene oxide to metal complex.

In certain embodiments, any of the above methods comprise ethylene oxide present in amounts between about 0.5 M to about 20 M. In certain embodiments, ethylene oxide is present in amounts between about 0.5 M to about 2 M. In certain embodiments, ethylene oxide is present in amounts between about 2 M to about 5 M. In certain embodiments, ethylene oxide is present in amounts between about 5 M to about 20 M. In certain embodiments, ethylene oxide is present in an amount of about 20 M. In certain embodiments, liquid ethylene oxide comprises the reaction solvent.

In certain embodiments, $CO_2$ is present at a pressure of between about 30 psi to about 800 psi. In certain embodiments, $CO_2$ is present at a pressure of between about 30 psi to about 500 psi. In certain embodiments, $CO_2$ is present at a pressure of between about 30 psi to about 400 psi. In certain embodiments, $CO_2$ is present at a pressure of between about 30 psi to about 300 psi. In certain embodiments, $CO_2$ is present at a pressure of between about 30 psi to about 200 psi. In certain embodiments, $CO_2$ is present at a pressure of between about 30 psi to about 100 psi. In certain embodiments, $CO_2$ is present at a pressure of between about 30 psi to about 80 psi. In certain embodiments, $CO_2$ is present at a pressure of about 30 psi. In certain embodiments, $CO_2$ is present at a pressure of about 50 psi. In certain embodiments, $CO_2$ is present at a pressure of about 100 psi. In certain embodiments, the $CO_2$ is supercritical.

In certain embodiments, any of the above methods comprise the reaction to be conducted at a temperature of between about 0° C. to about 100° C. In certain embodiments, the reaction is conducted at a temperature of between about 23° C. to about 100° C. In certain embodiments, the reaction to be conducted at a temperature of between about 23° C. to about 80° C. In certain embodiments, the reaction to be conducted at a temperature of between about 23° C. to about 50° C. In certain embodiments, the reaction to be conducted at a temperature of about 23° C.

In certain embodiments, the reaction step of any of the above methods does not further comprise a solvent.

However, in certain embodiments, the reaction step of any of the above methods does further comprise one or more solvents. In certain embodiments, the solvent is an organic solvent. In certain embodiments, the solvent is an organic ether. In certain embodiments, the solvent is an aromatic hydrocarbon. In certain embodiments the solvent is a ketone.

In certain embodiments suitable solvents include, but are not limited to: Methylene Chloride, Chloroform, 1,2-Dichloroethane, Propylene Carbonate, Acetonitrile, Dimethylformamide, N-Methyl-2-pyrrolidone, Dimethyl Sulfoxide, Nitromethane, Caprolactone, 1,4-Dioxane, and 1,3-Dioxane.

In certain other embodiments, suitable solvents include, but are not limited to: Methyl Acetate, Ethyl Acetate, Acetone, Methyl Ethyl Ketone, Propylene Oxide, Tretrahydrofuran, Monoglyme Triglyme, Propionitrile, 1-Nitropropane, Cyclohexanone.

In certain embodiments, the reaction step of any of the above methods produces ethylene carbonate (EC) as a by-product in amounts of less than about 20%. In certain embodiments, ethylene carbonate (EC) is produced as a by-product in amounts of less than about 15%. In certain embodiments, ethylene carbonate (EC) is produced as a by-product in amounts of less than about 10%. In certain embodiments, ethylene carbonate (EC) is produced as a by-product in amounts of less than about 5%. In certain embodiments, ethylene carbonate (EC) is produced as a by-product in amounts of less than about 1%. In certain embodiments, the reaction does not produce any detectable by-products (e.g., as detectable by $^1$H-NMR and/or liquid chromatography (LC)).

Tapered and Block Co-Polymers

As is understood from the above, the poly(ethylene carbonate) polymer is a co-polymer of units "Y" and "Z":

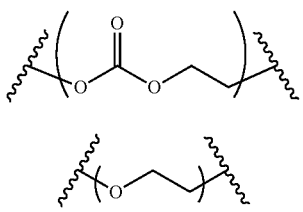

In certain embodiments, the poly(ethylene carbonate) polymer is a tapered co-polymer of units Y and Z (e.g., wherein the incorporation of Z increases or decreases along the length of a given polymer chain.):

In certain embodiments, the poly(ethylene carbonate) polymer is a block co-polymer of homopolymer units of Y and Z; the union of the homopolymer subunits may require an intermediate non-repeating subunit, known as a junction block. Block copolymers with two or three distinct blocks are called diblock copolymers and triblock copolymers, respectively.

In certain embodiments, the tapered or block co-polymer of poly(ethylene carbonate) is of the formula:

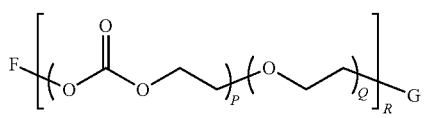

wherein each instance of P and Q are, independently, an integer of between about 10 to about 10,000, inclusive, and wherein R is an integer ranging from about 1 to about 20, each F and G are, independently, suitable terminating groups, as described above and herein.

For example, in certain embodiments, the present disclosure provides a method of making a poly(ethylene carbonate) block co-polymer, comprising the steps of (i) providing a polyethylene oxide (PEO) polymer, and (ii) reacting the polyethylene oxide polymer with ethylene oxide and carbon dioxide in the presence of a metal complex. In certain embodiments, the metal complex is a metal complex of formula (I), or any subset thereof.

In certain embodiments, the polyethylene oxide polymer of step (i) is provided by reacting ethylene oxide in the presence of a metal complex. In certain embodiments, the metal complex is a metal complex of formula (I), or any subset thereof.

In certain embodiments block copolymer compositions may be produced by varying or removing the $CO_2$ pressure during part of the polymerization process. When the CO2 pressure is low or non-existent, the catalyst will produce polymer having a higher degree of ether linkages than when the CO2 pressure is high. Thus, in certain embodiments of the present disclosure the polymerization may be initiated with any of the metal complexes described above at a relatively high $CO_2$ pressure (for example, higher than 100 psi, higher than about 200 psi, or higher than about 400 psi). These conditions will produce polymer having a predominance of carbonate linkages. After a length of time, the $CO_2$ pressure is lowered (for example to less than 100 psi, less than 50 psi, or to atmospheric pressure) or is removed completely. These conditions result in new block with more ether bonds being incorporated into the growing polymer chains. The above described process can optionally be repeated one or more times to build diblock, triblock or multiblock polymers. Additionally, several different $CO_2$ pressure levels can be used in the process to produce polymers with several different block types. In certain embodiments, the $CO_2$ pressure is initially low and is then increased. In certain other embodiments the $CO_2$ pressure is varied periodically. In certain other embodiments, the $CO_2$ pressure is varied smoothly over time to form tapered polyether co polycarbonate polymer compositions or blocks with a tapered copolymeric structure.

EXEMPLIFICATION

Example 1. Highly Active Cobalt Catalysts for Alternating Copolymerization of Ethylene Oxide and Carbon Dioxide The inventors have recently found that (salcy)CoOBzF$_5$ (salcy=N,N'-bis(3,5-di-tert-butylsalicylidene)-1,2-diaminocyclohexane; OBzF$_5$=pentafluorobenzoate; 1) efficiently copolymerizes cyclohexene oxide (CHO) or propylene oxide (PO) with $CO_2$. However, there has been no report using 1 for the copolymerization of EO and $CO_2$ to make PEC. Herein is reported the development of highly active Co(salcy) catalysts for the copolymerization of EO/$CO_2$ under low $CO_2$ pressure to produce copolymers with high carbonate percentages.

The recent success using 1 with bis(triphenylphosphoranylidene)ammonium chloride ([PPN]Cl) to copolymerize PO and $CO_2$ led us to investigate this catalytic system for the copolymerization of EO and $CO_2$ (Scheme 1 and Table 2) (see (a) Moore, D. R.; Cheng, M.; Lobkovsky, E. B.; Coates, G. W. Angew. Chem. Int. Ed. 2002, 41, 2599-2602. (b) Cheng, M.; Moore, D. R.; Reczek, J. J.; Chamberian, B. M.; Lobkovsky, E. B.; Coates, G. W. J. Am. Chem. Soc. 2001, 123, 8738-8749. (c) Cheng, M.; Lobkovsky, E. B.; Coates, G. W. J. Am. Chem. Soc. 1998, 120, 11018-11019. (d) Allen, S. D.; Moore, D. R.; Lobkovsky, E. B.; Coates, G. W. J. Am. Chem. Soc. 2002, 124, 14284-14285. (e) Qin, Z. Q.;

Thomas, C. M.; Lee, S.; Coates, G. W. *Angew. Chem. Int. Ed.* 2003, 42, 5484-5487. (f) Cohen, C. T.; Chu, T.; Coates, G. W. *J. Am. Chem. Soc.* 2005, 127, 10869-10878. (g) Cohen, C. T.; Coates, G. W. *J. Polym. Sci., Part A: Polym. Chem.* 2006, 44, 5182-5191).

Scheme 1.

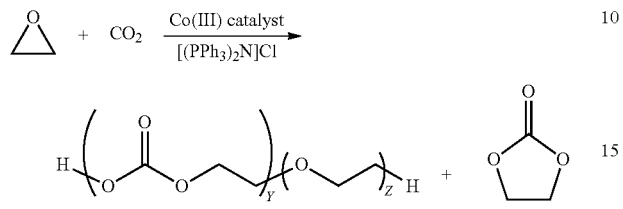

poly(ethylene carbonate-co-ethylene oxide)   EC by-product

TABLE 2

| Co Catalyst | $R^7$ | $R^9$ |
|---|---|---|
| 1 | t-Bu | t-Bu |
| 2 | —C(Me)(Et)$_2$ | t-Bu |
| 3 | —C(Et)$_3$ | t-Bu |
| 4 | —C(Me)$_2$CH$_2$C(Me)$_3$ | t-Bu |
| 5 | —C(Et)$_3$ | —CH$_3$ |
| 6 | —C(Et)$_3$ | i-Pr |
| 7 | —CH$_3$ | —C(Et)$_3$ |
| 8 | t-Amyl (—CH$_2$C(CH$_3$) | t-Amyl (—CH$_2$C(CH$_3$) |
| 9 | Cumyl (—C(CH$_3$)$_2$Ph) | Cumyl (—C(CH$_3$)$_2$Ph) |

—OBzF$_5$O=—O(C=O)C$_6$F$_5$

Co Catalysts (1-9)

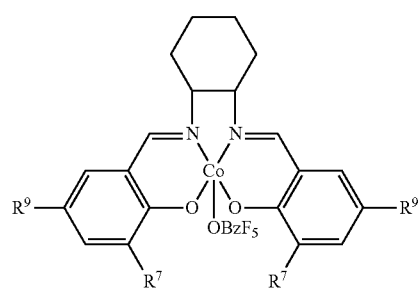

(10)

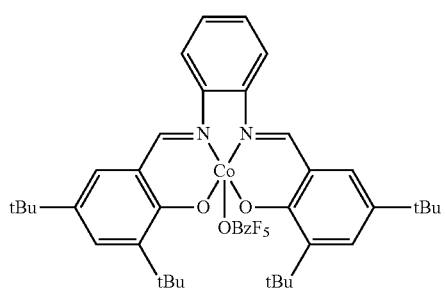

(11)

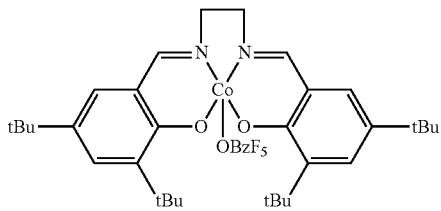

(12)

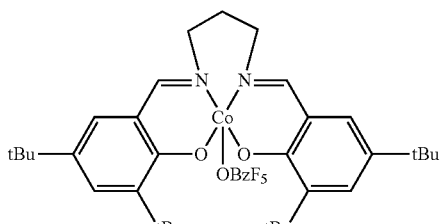

(13)

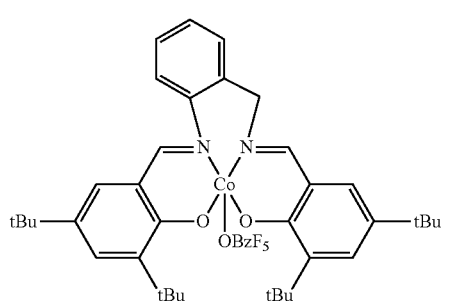

(14)

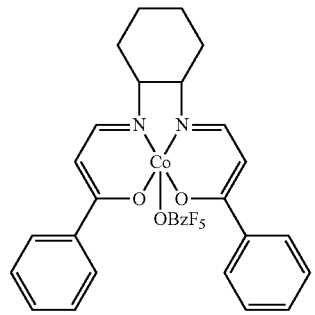

(15)

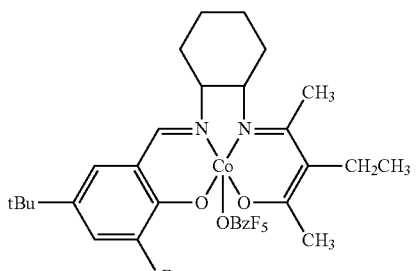

Reacting 1/[PPN]Cl with EO under 100 psi CO$_2$ at 22° C. produced a very viscous solution after just 1 hour, which suggested that 1/[PPN]Cl was active for EO/CO$_2$ copolymerization. Further analysis of the product revealed poly (EO-co-EC) had been synthesized (entry 1, Table 3).

The $^1$H NMR spectrum of the polymer produced by 1/[PPN]Cl is shown in FIG. 1A. In addition to the expected polycarbonate peak (a), shifts were also observed which correspond to ether linkages (b, c, d), indicating that the copolymerization under these conditions is not perfectly alternating. Ether incorporation is problematic because it negatively affects the gas barrier properties. Despite many changes in the reaction conditions, we were unable to completely suppress ether incorporation using catalyst 1.

TABLE 3

Experimental Conditions and Results of Copolymerization of EO and $CO_2$[a]

| entry | catalyst | [Co] (mM) | yield[b] (%) | TOF[c] (h$^{-1}$) | carbonate[d] (%) | PEC:EC[e] (% PEC) | $M_n$[f] (g/mol) | $M_w/M_n$[f] |
|---|---|---|---|---|---|---|---|---|
| 1 | 1 | 10 | 47 | 940 | 67 | 83 | 25,900 | 1.6 |
| 2[g] | 1 | 10 | 21 | 830 | 85 | 99 | 14,100 | 1.4 |
| 3 | 1 | 5.0 | 21 | 830 | 89 | 97 | 36,700 | 1.4 |
| 4[h] | 1 | 2.0 | 16 | 520 | 93 | >99 | 34,800 | 1.5 |
| 5[i] | 1 | 5.0 | 19 | 760 | 90 | 99 | 24,400 | 1.3 |
| 6[j] | 1 | 5.0 | 13 | 510 | 89 | 99 | 15,700 | 1.3 |
| 7[k] | 1 | 10 | 26 | 170 | 84 | >99 | 22,800 | 1.2 |
| 8[l] | 1 | 5.0 | 46 | 610 | 76 | 99 | 29,800 | 1.5 |
| 9 | 2 | 10 | 41 | 820 | 99 | 93 | 28,900 | 1.3 |
| 10 | 3 | 10 | 27 | 540 | >99 | 95 | 32,400 | 1.3 |
| 11 | 4 | 10 | 20 | 400 | >99 | 95 | 27,100 | 1.4 |
| 12 | 5 | 10 | 13 | 250 | >99 | 68 | 28,100 | 1.4 |
| 13 | 6 | 10 | 26 | 530 | >99 | 86 | 26,500 | 1.3 |
| 14 | 7 | 10 | 34 | 680 | 98 | 91 | 26,100 | 1.4 |
| 15 | 8 | 10 | 45 | 910 | 97 | 94 | 33,700 | 1.4 |
| 16 | 9 | 10 | 22 | 430 | >99 | 80 | 26,000 | 1.4 |
| 17 | 10 | 10 | 27 | 540 | 92 | 81 | 29,400 | 1.5 |

[a]Polymerizations run in neat ethylene oxide (EO); $[EO]_0 = 20M$; $[Co]_0 = [[PPN]Cl]_0$; with 100 psi of $CO_2$ at 22° C. for 1 h.
[b]Determined by crude products mass assuming that both PEC and EC are present.
[c]Turnover frequency = mol PEC/mol Co · h.
[d]Determined by $^1$H NMR spectroscopy of the purified copolymer.
[e]Determined by $^1$H NMR spectroscopy of PEC and EC of the crude product.
[f]Determined by gel permeation chromatography calibrated with PMMA standards in DMF.
[g]30 min.
[h]3 h.
[i]$P_{CO_2}$ = 80 psi.
[j]$P_{CO_2}$ = 50 psi.
[k]0° C. for 3 h.
[l]$[EO]_0$ = 10M in 1,4-dioxane for 1.5 h.

In order to achieve a perfectly alternating copolymerization, the catalyst structure was optimized by varying ligand substituents. Several catalysts were prepared by changing $R^7$ and/or $R^9$ (Scheme 1), and screened for $EO/CO_2$ copolymerization (Table 3). Catalysts 1-10 were active for the copolymerization and their activities were influenced by the substituents $R^7$ and $R^9$. With tert-butyl groups at $R^7$ and $R^9$ (1), the copolymerization proceeded rapidly to give 47% EO conversion in 1 hour with a high turnover frequency (TOF) (entry 1). After 1 hour, the copolymerization solution was very viscous, preventing the dissolution of $CO_2$ and effectively stopping the polymerization. In addition, back biting occurred to produce 17% ethylene carbonate (EC) (entry 1). Reducing the reaction time to 30 min kept viscosity low, thus reduced back biting and increased carbonate percentage (entry 2). Compared with 1, 2 bearing bulkier substituents at $R^1$ gave a copolymer with higher carbonate percentage, although the catalytic activity slightly decreased (entry 9). This suggested the bulkiness of the $R^7$ substituent significantly impacts carbonate percentage. Complexes 3 and 4 produced nearly perfect alternating PEC (entry 10 and 11). The carbonate content followed the trend 1<2<3<4 and the activity trend was 1>2>3>4. This demonstrates that carbonate percentage increases with steric bulk while activity decreases.

The effects of changing $R^9$ were also examined. Catalyst 5, bearing a Me group, afforded the slowest polymerization resulting a TOF of 250 h$^{-1}$, however, the resulting copolymer exhibited very high carbonate percentage, 99.1% (entry 12). Complex 6 where $R^9$=i-Pr showed similar catalytic activity and similar carbonate percentage as complex 3 (entry 13). This observation suggests that the substituent $R^9$ does not significantly influence the carbonate percentage but does influence the rate.

Complex 7, which has a small substituent at $R^7$ and a bulky substituent at $R^9$, was expected to show high activity and low carbonate percentage in the resulting copolymer. The catalytic activity was relatively high, however, to our surprise, 98% carbonate percentage was obtained regardless of the small substituent at $R^7$. This result suggests that the larger substituents for $R^7$ and $R^9$ improve the activity and the carbonate percentage.

Complexes 8 and 9 were rapidly prepared from commercially available disubstituted phenols and were also evaluated for the copolymerization. Catalyst 8 exhibited a high TOF of 910 h$^{-1}$ comparable to 1 and gave higher carbonate percentage of 96.8% (entry 15). Catalyst 9 gave a TOF of 430 h$^{-1}$, which is slower than 1 and 8. However, 9 gave very high carbonate percentage of 99.1% (entry 16). Among these three catalysts, the least sterically hindered compound 1, gave the highest activity and the lowest carbonate percentage, while the most sterically hindered compound 9, gave the lowest activity but the highest carbonate percentage. This mirrors the trend observed with compounds 1-4.

We also screened 10, which is identical to 1, but has a phenyl backbone in place of the cyclohexyl. A similar version of this catalyst, with an acetate initiator, induces the stereoselective homopolymerization of PO to give perfectly isotactic poly(propylene oxide). The catalytic activity and the carbonate linkage content were 540 h$^{-1}$ and 92.1%, respectively, not as high active as with 1, although the structure is very similar to that of 1 (entry 17).

Reducing the concentration of 1 caused a decrease in the catalytic activity but an increase of the carbonate linkage (entry 3 and 4). This result suggests that the insertion rates of EO to alkoxide and carbonate termini in the copolymer depend on the Co concentration, and the EO insertion may involve a bimetallic mechanism of the catalyst.

Copolymerizations were also performed by filling $CO_2$ into the solution of EO, Co catalyst, and cocatalyst (PPNCl) under 30-400 psi at room temperature to give poly(ethylene carbonate) (PEC). The catalystic activities were higher than those of other catalyst to give ca. 100 g-polymer/g-catalyst·h (for catalyst 1). The catalytic activities were compared among the catalysts 2, 8, 9 (Table 4). It proved that the more bulky substituent in the catalyst, the less active.

TABLE 4

Comparison of Co catalyst[a]

| Catalyst | Yield, % | TOF, h$^{-1}$ | Activity, g-polymer/g-cat · h | Carbonate Linkage, % |
|---|---|---|---|---|
| 1 | 44.3 | 886 | 95.7 | 66.0 |
| 8 | 42.2 | 844 | 85.3 | 96.7 |
| 9 | 21.5 | 430 | 35.7 | 99.1 |
| 2 | 38.1 | 762 | 77.0 | 98.9 |

[a]EO = 100 mmol, Co cat = 0.050 mmol, PPNCl = 0.050 mmol, $P_{CO2}$ = 100 psi, Polymerization time = 1 h.

The effect of the catalyst concentration (of catalyst 1) to the catalytic activity was also investigated. As shown in Table 5, the catalytic activity increased with the catalyst 1 concentration.

TABLE 5

Effect of Catalyst Concentration[a]

| [Co 1]$_0$, mM | Reaction Time, h | Yield, % | TOF, h$^{-1}$ | Activity, g-polymer/g-cat · h | Carbonate Linkage, % |
|---|---|---|---|---|---|
| 1.0 | 2 | 3.1 | 310 | 32.6 | 93.2 |
| 5.0 | 2.5 | 37.7 | 602 | 64.4 | 85.2 |
| 9.1 | 1 | 31.9 | 708 | 74.8 | 71.6 |
| 10 | 1 | 44.3 | 886 | 95.7 | 66.0 |

[a] [EO]$_0$ = 20M (bulk), [Co]$_0$ = [PPNCl]$_0$, P$_{CO2}$ = 100 psi.

Table 5 shows the effect of CO$_2$ pressure to catalytic activity of catalyst 1. The activity increased with the pressure at low pressure. However, it had a maximum about 200 psi.

TABLE 6

Effect of CO$_2$ Pressure[a]

| P$_{CO2}$ | Reaction Time, h | Yield, % | TOF, h$^{-1}$ | Activity, g-polymer/g-cat · h | Carbonate Linkage, % |
|---|---|---|---|---|---|
| 50 | 4 | 4.1 | 203 | 19.9 | 96.0 |
| 100 | 2 | 3.1 | 310 | 32.6 | 93.2 |
| 200 | 3 | 9.1 | 606 | 62.9 | 74.4 |
| 400 | 2 | 2.8 | 278 | 29.2 | 64.9 |

[a] [EO]$_0$ = 20M (bulk), [Co 1]$_0$ = [PPNCl]$_0$ = 1.0 mM.

Figure 1B:
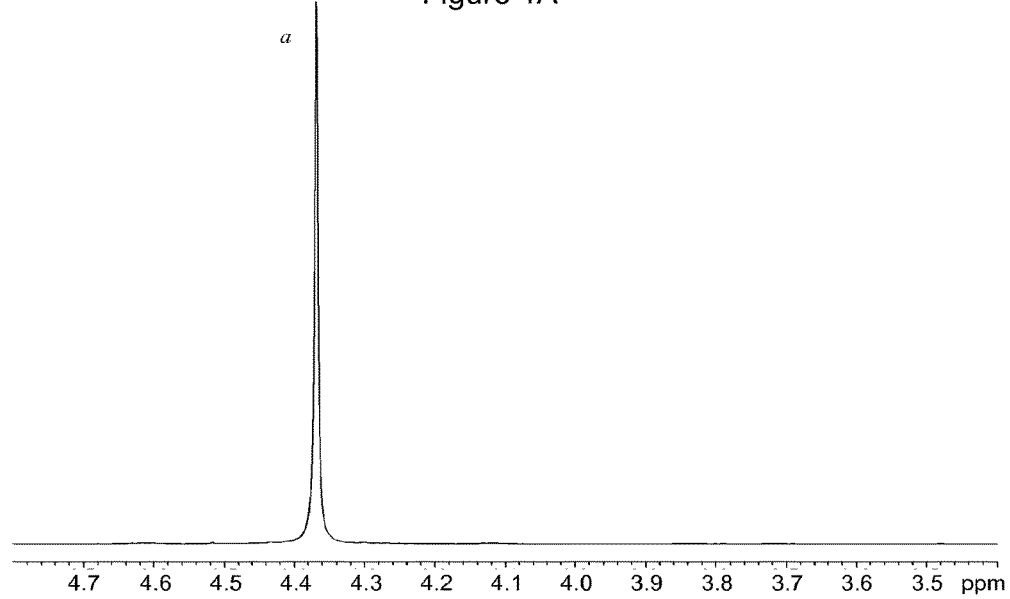
FIG. 1B. $^1$H NMR spectra (300 MHz) of PEC obtained by catalyst 4 in conjunction with [PPN]Cl.
Figure 2:
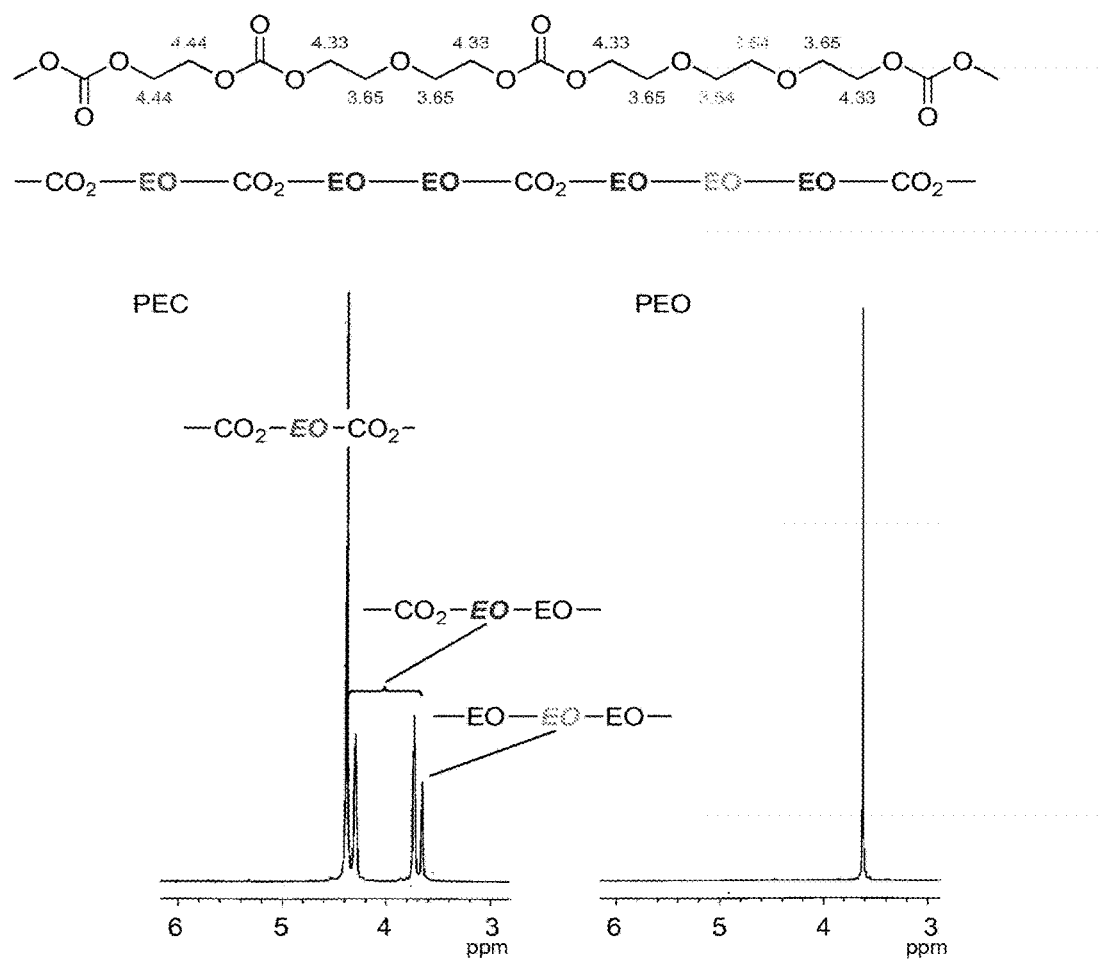
FIG. 2. $^1$H NMR spectra of PEC and PEO.

From $^1$H NMR analysis, the obtained polymers mainly consist of carbonate linkage but have some amount of ether linkage, which depended on the reaction conditions (catalyst concentration, CO$_2$ pressure, and reaction temperature) and substituents of the catalyst (see FIGS. 1 and 2). The most active catalyst 1 had the least carbonate linkage and the least active catalyst 2 had the highest carbonate linkage. Especially, the catalyst 2 produced almost perfect PEC. The effect of the catalyst concentration to the carbonate linkage were also shown in Table 5. It showed that the carbonate linkage increased by decreasing the catalyst concentration. The CO$_2$ pressure also affected the carbonate linkage. Opposite to expected, the carbonate linkage decreased by increasing the pressure as shown in Table 6.

Catalyst 15 has also been found to be effective to provide a poly(ethylene carbonate-co-ethylene oxide) polymer.

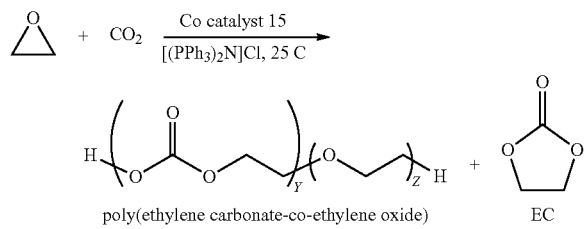

poly(ethylene carbonate-co-ethylene oxide)    EC

EO:CO:PPNCl=2000:1:1; PCO$_2$=100 psi; 3 hr; 14% yield of polymer; TOF=92 h$^{-1}$; carbonate linkage 96%; PEC:EC=93:7.

In conclusion, we have reported the first examples of Co-catalyzed EO/CO$_2$ copolymerization. The polymerizations were very fast even under relatively low pressure. The obtained copolymer consists not only of carbonate linkages but also ether linkages which indicates both EO/CO$_2$ alternating copolymerization and EO homopolymerization are occurring during the copolymerization. The ether content can be decreased through the catalyst design. Catalyst 3 gave a high catalytic activity and a copolymer with the greatest carbonate content, which is almost a perfectly alternating copolymer.

Example 2. Polymerization of Ethylene Oxide (PEO)

Figure 3:
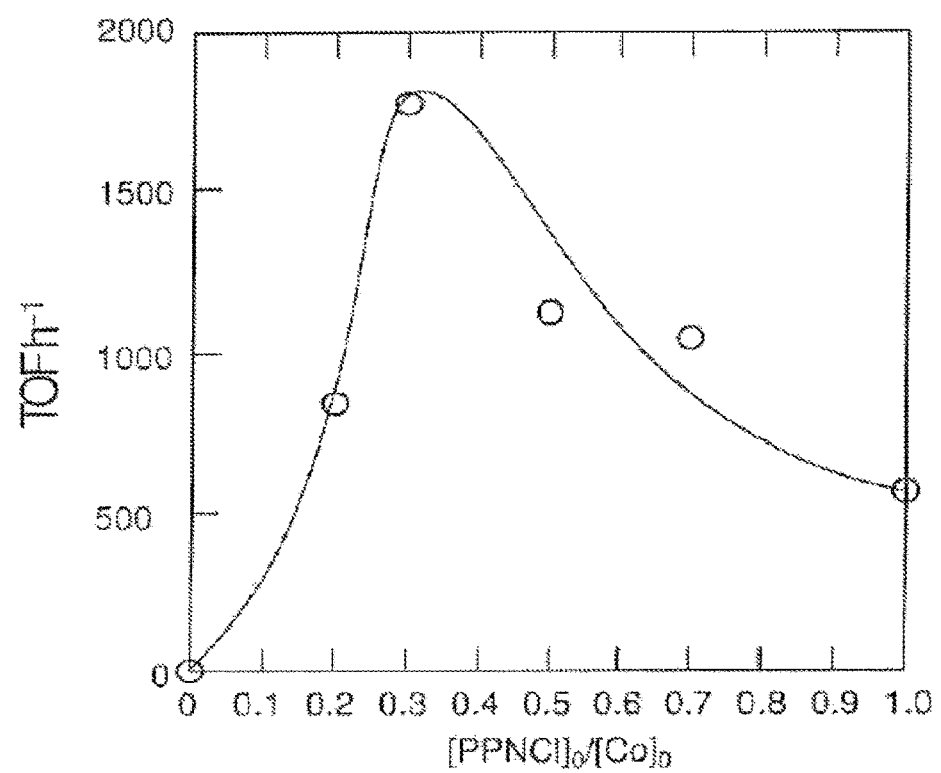
FIG. 3. (Salcy)CoOBzF$_5$ induced ethylene oxide (EO) polymerization in the presence of PPNCl. The catalytic activity is strongly dependant on the PPNCl/Co ratio.

(Salcy)CoOBzF$_5$ induced ethylene oxide (EO) polymerization in the presence of PPNCl. The activity was strongly depended on the PPNCl/Co ratio (see Table 7 and FIG. 3).

Scheme 2.

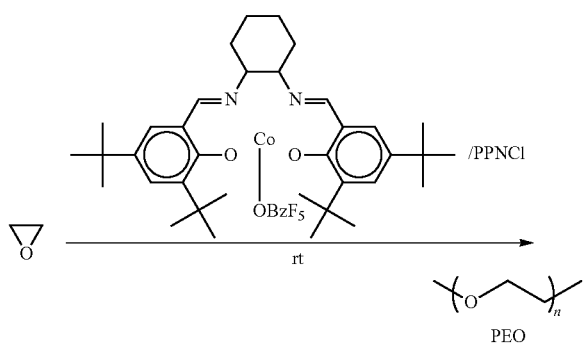

TABLE 7

Effect of [PPNCl]/[Co]

| [PPNCl]/[Co] | Product Mass, g | Yield, % | TOF, h$^{-1}$ |
|---|---|---|---|
| 0.2 | 0.1535 | 3.5 | 836 |
| 0.3 | 0.3252 | 7.4 | 1777 |
| 0.5 | 0.2065 | 4.7 | 1125 |
| 0.7 | 0.1917 | 4.4 | 1044 |
| 1 | 0.1030 | 2.3 | 561 |

[EO]$_0$ = 20M, [Co]$_0$ = 5.0 mM, [PPNCl]$_0$ = 1.0-5.0 mM, rt 10 min.

Example 3. Synthesis of Block Copolymer of PEO-b-PEC

Figure 4A:
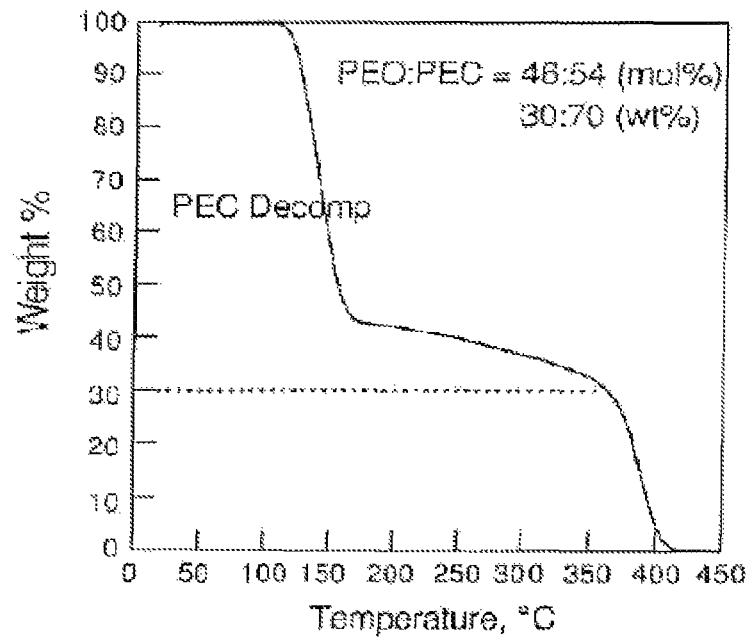
FIG. 4A. TGA analyses of PEO-b-PEC.
Figure 4B:
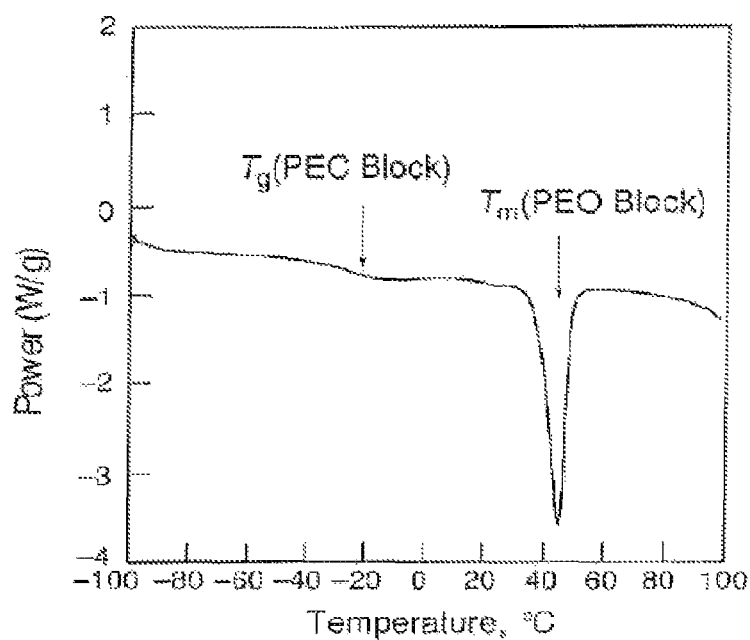
FIG. 4B. DSC (FIG. 4B) analyses of PEO-b-PEC.

The one-pot PEO-b-PEC synthesis was then examined. PEO was polymerized in a glass autoclave first, and then the reaction solution was pressurized with CO$_2$ to undergo EO/CO$_2$ copolymerization. This polymer consists of hard segment (PEO)/soft segment (PEC), and is thus considered to have a new function (see FIGS. 4A-4B depicting the TGA and DSC analyses of PEO-b-PEC).

Scheme 3.

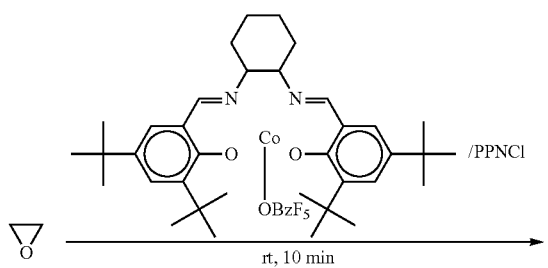

-continued

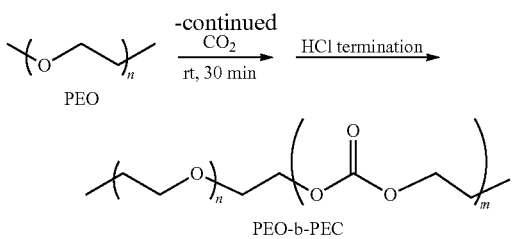

PEO-b-PEC

Other Embodiments

The foregoing has been a description of certain non-limiting preferred embodiments. Those of ordinary skill in the art will appreciate that various changes and modifications to this description may be made without departing from the spirit or scope of the present disclosure, as defined in the following claims.

We claim:

1. A method of synthesizing a poly(ethylene carbonate) polymer, wherein the polymer is made up of Y, and optionally Z, the percentage of Y is greater than the percentage of Z, and the polymer has greater than 95% of Y,

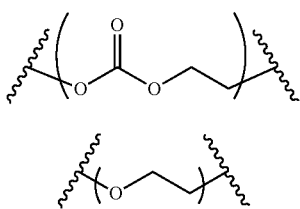

Y

Z

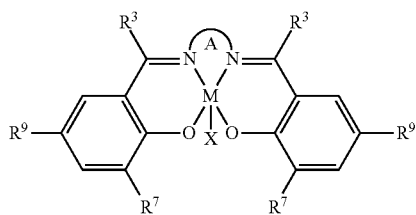

the method comprising reacting ethylene oxide and carbon dioxide in the presence of a metal complex, wherein the metal complex is of the formula:

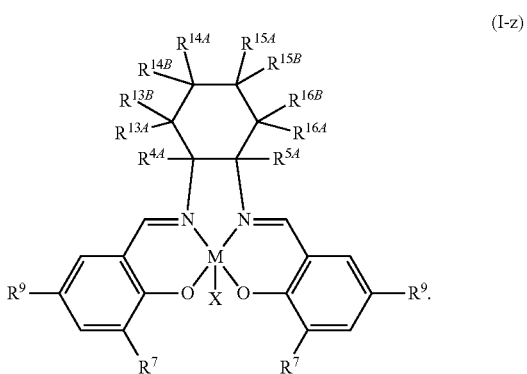

wherein:

M is a metal selected from zinc, cobalt, chromium, aluminum, titanium, ruthenium or manganese;

X is absent or is a nucleophilic ligand;

each instance of $R^3$ is, independently, selected from hydrogen, halogen, optionally substituted aliphatic, optionally substituted heteroaliphatic, optionally substituted aryl, and optionally substituted heteroaryl;

$R^7$ and $R^9$ are, independently, selected from hydrogen, halogen, —$OR^c$, —$OC(=O)R^c$, —$OC(=O)OR^c$, —$OC(=O)N(R^d)_2$, —$OSO_2R^d$, —$C(=O)OR^c$, —$C(=O)N(R^d)_2$, —CN, —CNO, —$N_3$, —$NO_2$, —$N(R^d)_2$, —$N(R^d)C(=O)OR^c$, —$N(R^d)C(=O)R^c$, —$N(R^d)SO_2R^d$, —$SO_2R^d$, —$SOR^d$, —$SO_2N(R^d)_2$, optionally substituted aliphatic, optionally substituted heteroaliphatic, optionally substituted aryl, optionally substituted heteroaryl, wherein each instance of $R^c$ is, independently, optionally substituted aliphatic, optionally substituted heteroaliphatic, optionally substituted aryl, optionally substituted heteroaryl, and each instance of $R^d$ is, independently, hydrogen, optionally substituted aliphatic, optionally substituted heteroaliphatic, optionally substituted aryl, optionally substituted heteroaryl;

wherein the A value of at least one of $R^7$ and $R^9$ is greater than the A-value of tert-butyl; and Ring A forms an optionally substituted 5- to 6-membered ring.

2. The method according to claim 1, wherein the metal complex is of the formula:

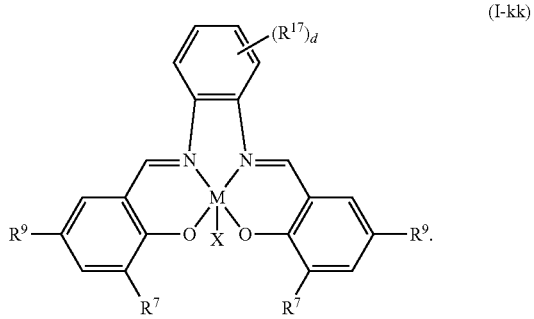

3. The method according to claim 1, wherein the metal complex is of the formula:

4. The method according to claim 1, wherein $R^7$ is an optionally substituted $C_{1-10}$ aliphatic group.

5. The method according to claim 1, wherein $R^7$ is an optionally substituted $C_{1-10}$ alkyl group.

6. The method according to claim 1, wherein $R^7$ is selected from methyl, trichloromethyl, trifluoromethyl, ethyl, n-propyl, isopropyl, t-butyl, sec-butyl, iso-butyl, n-pentyl, neopentyl, amyl, trityl, adamantyl, thexyl, benzyl and cumyl.

7. The method according to claim 1, wherein $R^9$ is an optionally substituted $C_{1-10}$ aliphatic group.

8. The method according to claim 1, wherein $R^9$ is an optionally substituted $C_{1-10}$ alkyl group.

9. The method according to claim 1, wherein $R^9$ is selected from methyl, trichloromethyl, trifluoromethyl, ethyl, n-propyl, isopropyl, t-butyl, sec-butyl, iso-butyl, n-pentyl, neopentyl, amyl, trityl, adamantyl, thexyl, benzyl and cumyl.

10. The method according to claim 1, wherein the A-value of $R^9$ is between about 0 to about 2.5 kcal/mol.
11. The method according to claim 1, wherein the metal complex is selected from any of the following formulae:
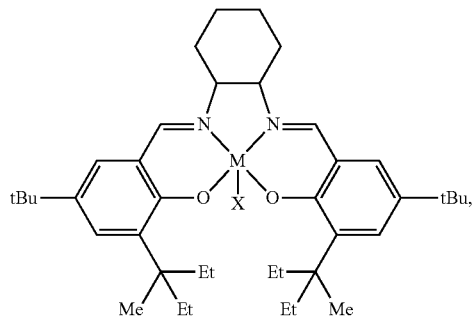
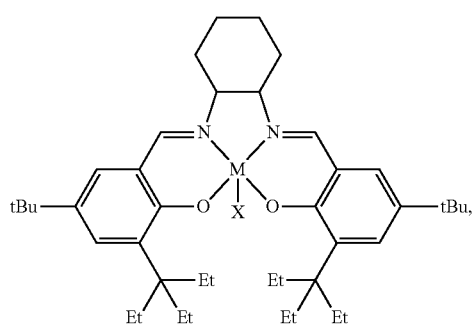
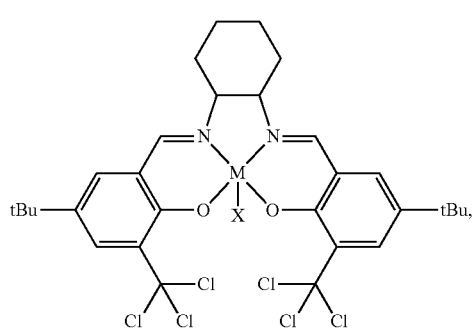
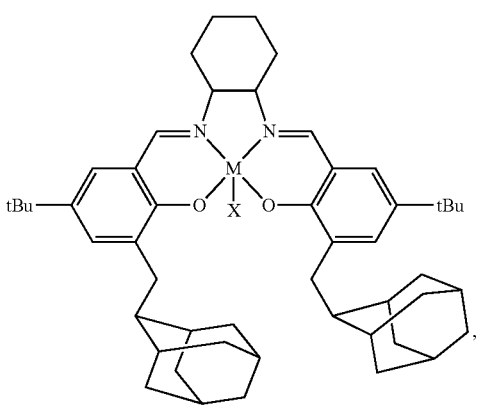
-continued
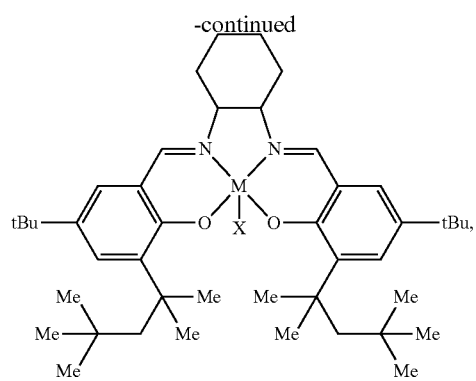
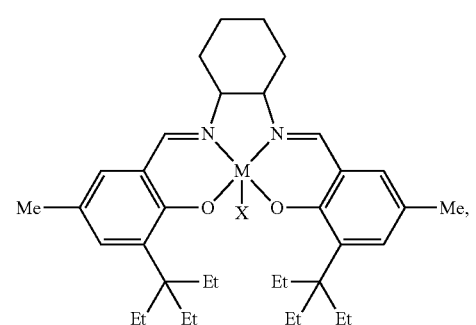
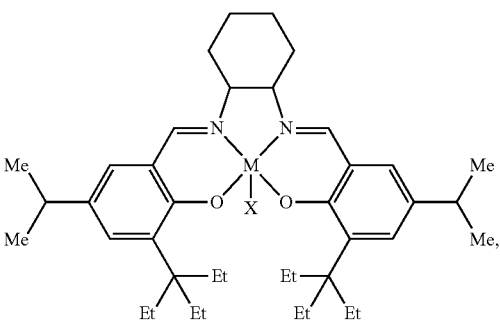
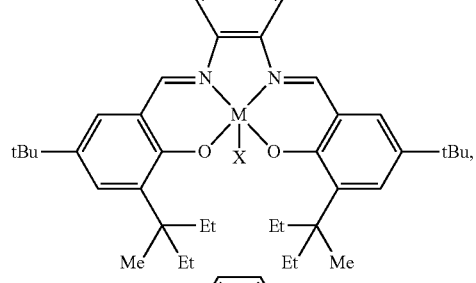
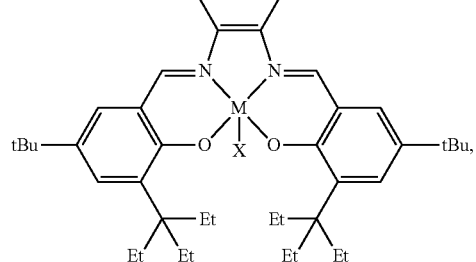

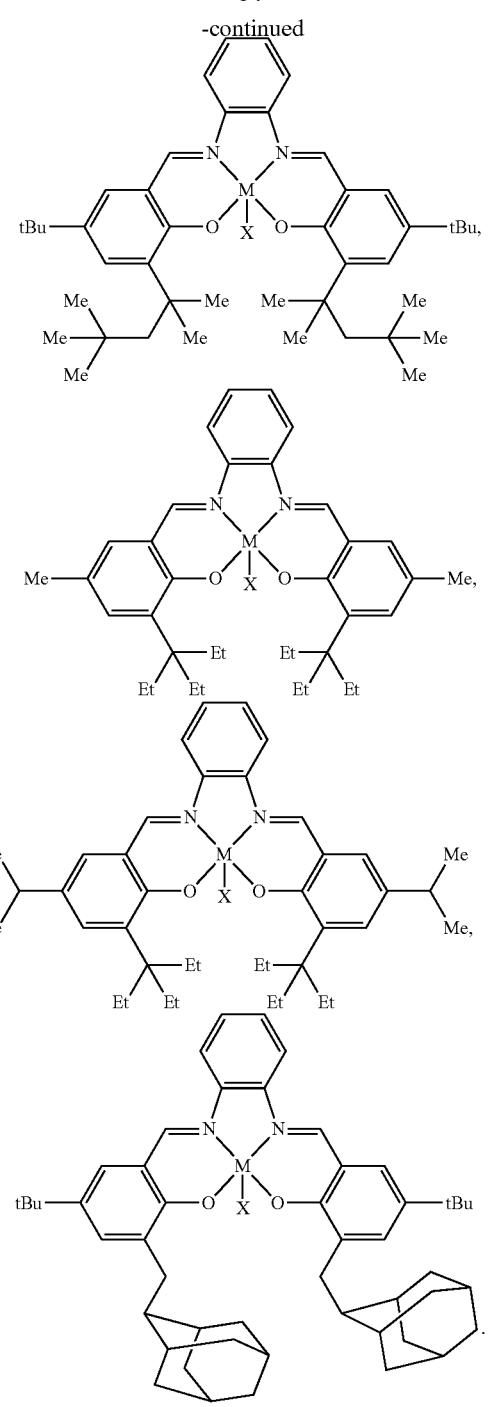

15. The method according to claim 14, wherein X is —O(C=O)C₆F₅.

16. The method according to claim 1, wherein the reaction further comprises a co-catalyst, wherein the co-catalyst is a salt.

17. The method according to claim 16, wherein the salt is an ammonium, phosphonium, or arsonium salt.

18. The method according to claim 17, wherein the ammonium salt is (n-Bu)₄NCl, (n-Bu)₄NBr, (n-Bu)₄NN₃, [PPN]Cl, [PPN]Br, or [PPN]N₃.

19. The method according to claim 1, wherein the polymer has greater than about 99% of Y.

20. The method according to claim 19, wherein the polymer is 100% of Y and 0% of Z.

21. The method according to claim 1, wherein the polymer is of the formula:

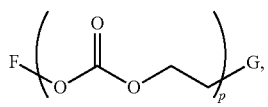

P is an integer of between about 10,000 and about 15,000, inclusive; and

F and G are, independently, suitable terminating groups.

22. A method of synthesizing a poly(ethylene carbonate) polymer, comprising a step of reacting ethylene oxide with carbon dioxide in the presence of a cobalt complex, wherein the cobalt complex is any one of the formulae:

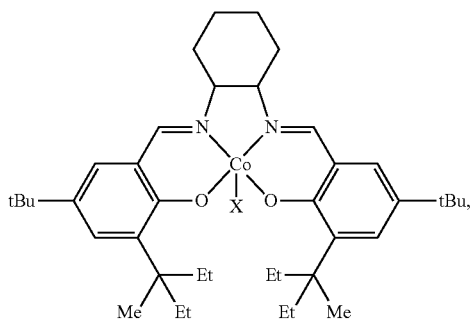

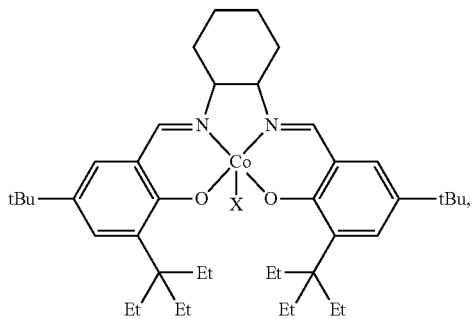

12. The method according to claim 1, wherein M is cobalt.

13. The method according to claim 1, wherein X is absent or is selected from the group consisting of: —ORˣ, —SRˣ, —O(C=O)Rˣ, —O(C=O)ORˣ, —O(C=O)N(Rˣ)₂, —N(Rˣ)(C=O)Rˣ, —NC, —CN, halo, —N₃, —O(SO₂)Rˣ and —OPRˣ, wherein each Rˣ is, independently, selected from hydrogen, optionally substituted aliphatic, optionally substituted heteroaliphatic, optionally substituted aryl and optionally substituted heteroaryl.

14. The method according to claim 1, wherein X is —O(C=O)C₆F₅, —O(C=O)C₆H₅, —O(C=O)CF₃, —O(C=O)CH₃, —NC, —CN, —N₃, —Cl, or —Br.

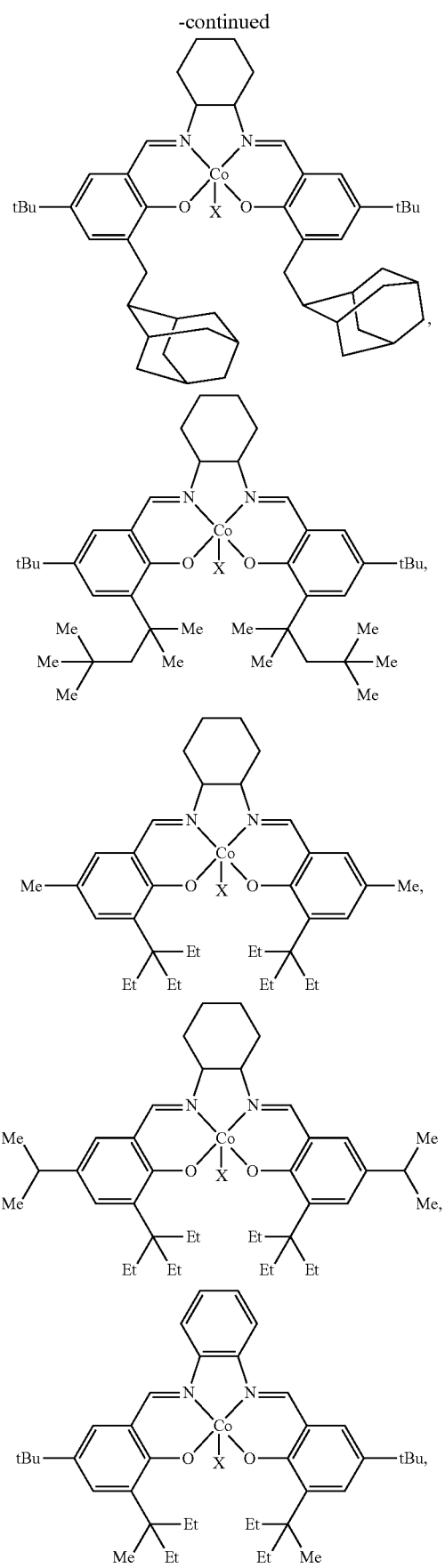
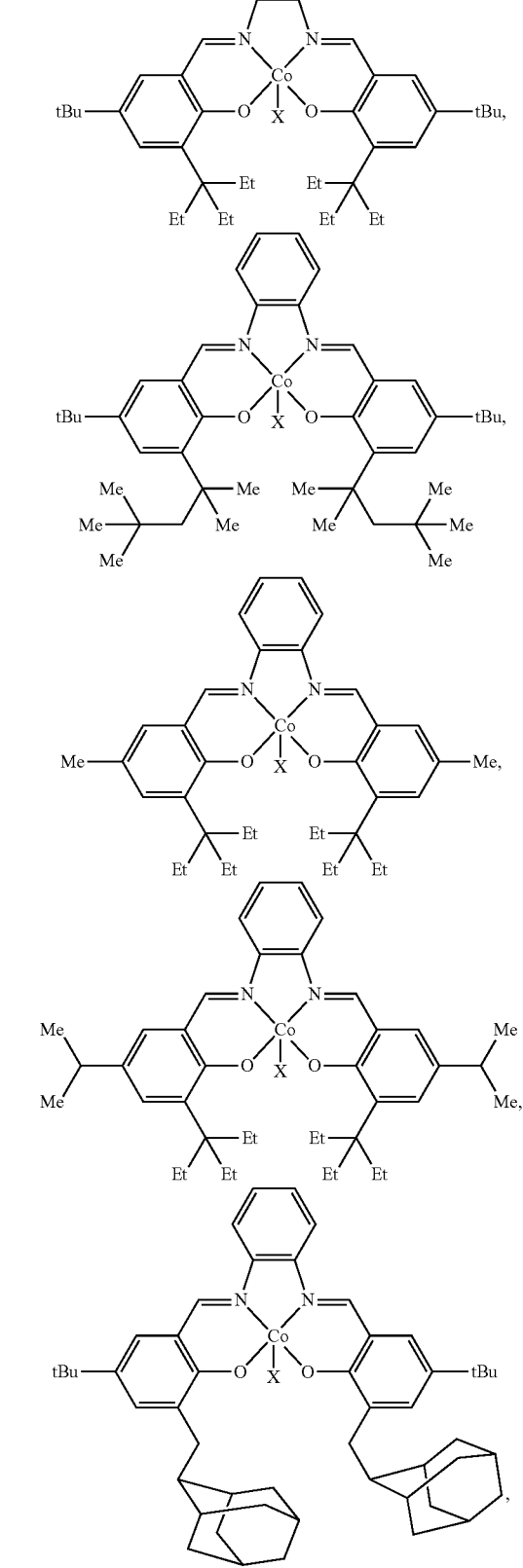
wherein X is absent or is a nucleophilic ligand; and wherein the polymer has greater than 95% carbonate linkages.

23. A metal complex of the formula:

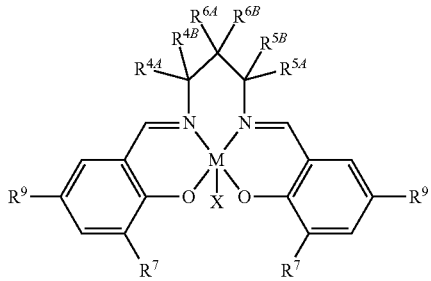

wherein:

M is a metal selected from zinc, cobalt, chromium, aluminum, titanium, ruthenium or manganese;

X is absent or is a nucleophilic ligand;

$R^7$ and $R^9$ are, independently, selected from hydrogen, optionally substituted aliphatic, optionally substituted heteroaliphatic, optionally substituted aryl, optionally substituted heteroaryl;

wherein the A value of at least one of $R^7$ and $R^9$ is greater than the A-value of tert-butyl; and $R^{4A}$, $R^{4B}$, $R^{5A}$, $R^{5B}$, and $R^{6A}$, $R^{6B}$ are, independently, selected from hydrogen, halogen, optionally substituted aliphatic, optionally substituted heteroaliphatic, optionally substituted aryl, optionally substituted heteroaryl, and/or, $R^{4A}$ and $R^{4B}$, and/or $R^{5A}$ and $R^{5B}$, and/or and $R^{6A}$ and $R^{6B}$ are optionally joined to form an oxo (=O) group, an oxime (=NOR$^a$) group, an imine (=NN(R$^a$)$_2$) group, an alkenyl (=C(R$^b$)$_2$) group, and/or a 3- to 6-membered spirocyclic ring, wherein each instance of R$^a$ and R$^b$ is, independently, hydrogen or optionally substituted aliphatic, wherein optionally two R$^a$ groups or two R$^b$ groups are joined to form a 3- to 6-membered ring.

24. The method of claim 1, wherein $R^7$ and $R^9$ are the same.

25. The method of claim 1, wherein $R^7$ and $R^9$ are different.

* * * * *